US009174251B2

(12) United States Patent
Dahlberg et al.

(10) Patent No.: US 9,174,251 B2
(45) Date of Patent: Nov. 3, 2015

(54) CLEANING PROCESS FOR A TEST DEVICE, COMPUTER PROGRAM PRODUCT FOR PERFORMING SUCH A PROCESS, AND TEST DEVICE

(75) Inventors: Martin Dahlberg, Bovenden (DE); Hartmut Langer, Goettingen (DE); Jens Meyer, Moringen (DE); Sven-Oliver Otto, Goettingen (DE)

(73) Assignee: Sartorius Stedim Biotech GMBH (DE)

( * ) Notice: Subject to any disclaimer, the term of this patent is extended or adjusted under 35 U.S.C. 154(b) by 973 days.

(21) Appl. No.: 13/089,550

(22) Filed: Apr. 19, 2011

(65) Prior Publication Data

US 2011/0265820 A1 Nov. 3, 2011

(30) Foreign Application Priority Data

Apr. 30, 2010 (DE) .......................... 10 2010 018 881

(51) Int. Cl.
*B08B 9/00* (2006.01)
*B08B 9/032* (2006.01)

(52) U.S. Cl.
CPC .............. *B08B 9/0328* (2013.01); *B08B 9/032* (2013.01); *B08B 9/0321* (2013.01); *B08B 9/0325* (2013.01); *Y10T 137/4252* (2015.04); *Y10T 137/8593* (2015.04)

(58) Field of Classification Search
CPC ....................................................... B08B 9/325
See application file for complete search history.

(56) References Cited

U.S. PATENT DOCUMENTS

2004/0211445 A1* 10/2004 Von Der Hardt et al. .... 134/22.1

FOREIGN PATENT DOCUMENTS

DE          101 35 785        2/2003
JP         410225628 A  *   8/1998  ............ B01D 65/10

OTHER PUBLICATIONS

Preparative and Process-Scale Liquid Chromatography—p. 60—Technical structure of liquid chromatography separation plants.
FDA U.S. Food and Drug Administration—Inspection Guides—Sterile Drug Substance Manufactures—pp. 1-5.

* cited by examiner

*Primary Examiner* — Michael Barr
*Assistant Examiner* — Jason Riggleman
(74) *Attorney, Agent, or Firm* — Gerald E. Hespos; Michael J. Porco; Matthew T. Hespos

(57) ABSTRACT

A cleaning process is provided for a test apparatus that has a switch, external connections and internal volumes that can come into contact with a fluid from a filter to be tested or a container to be tested. The cleaning process includes selecting one or more internal volumes to be cleaned, cleaning the selected internal volumes with a cleaning fluid by a corresponding switching of the switch, at least partially draining the cleaning fluid left in the selected internal volumes after cleaning, and flushing the selected internal volumes with a flushing fluid different from the cleaning fluid. Also provided are a computer program product for performing the cleaning process, a cleaning apparatus, and a test apparatus for testing filters and containers.

8 Claims, 9 Drawing Sheets

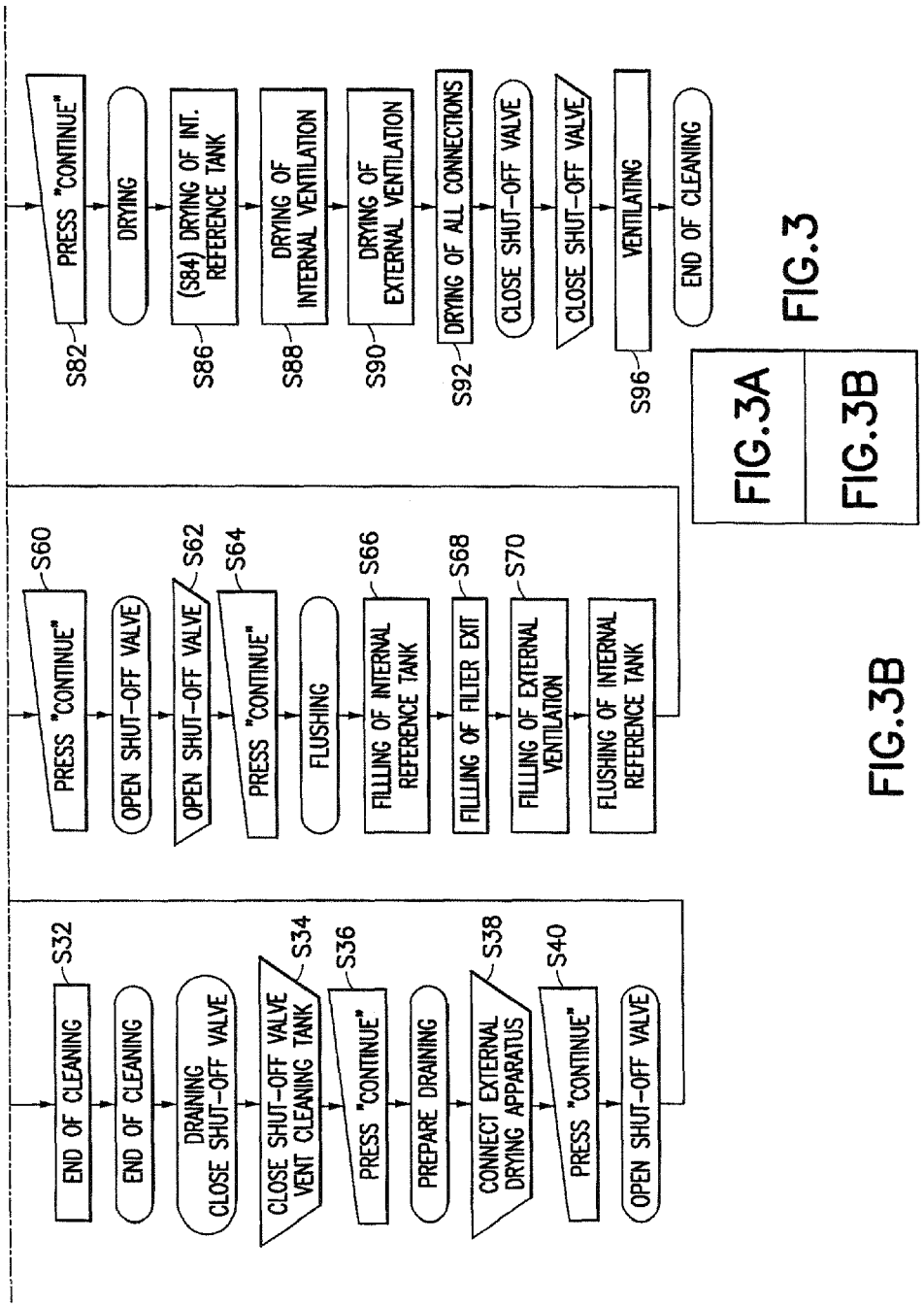

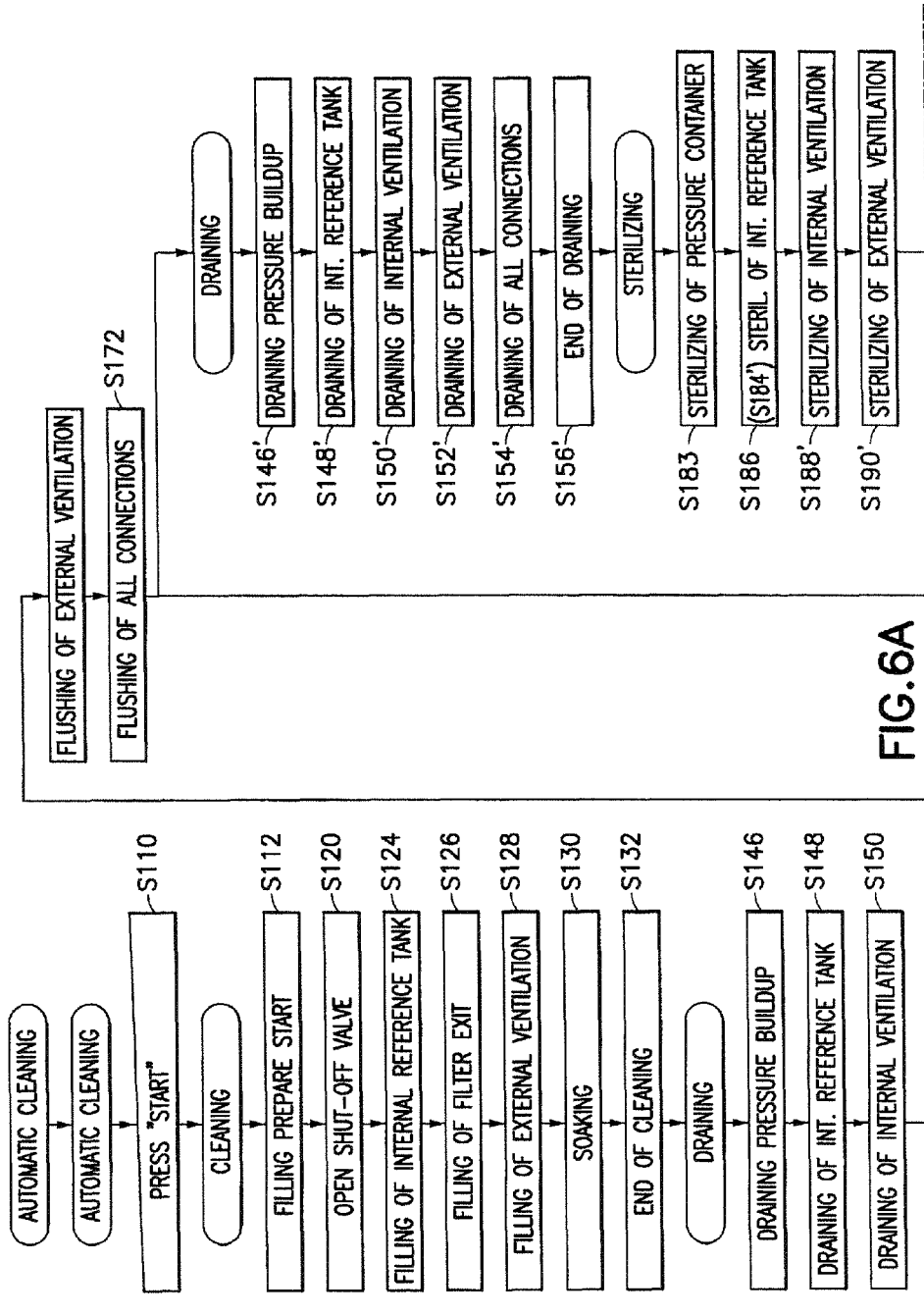

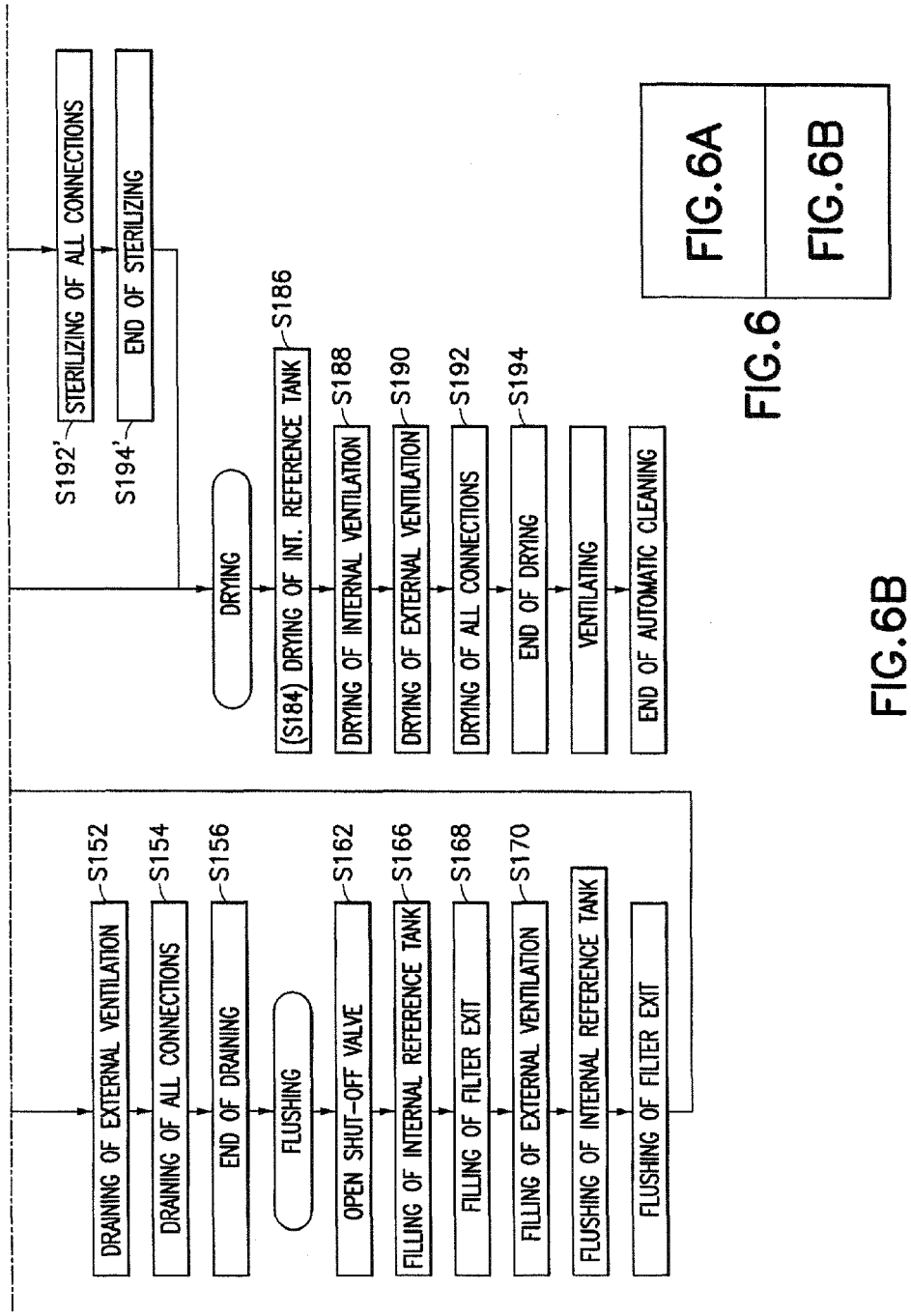

CLEANING PROCESS FOR A TEST DEVICE, COMPUTER PROGRAM PRODUCT FOR PERFORMING SUCH A PROCESS, AND TEST DEVICE

BACKGROUND OF THE INVENTION

1. Field of the Invention

The present invention relates to a cleaning process for a test apparatus, a computer program product for performing a cleaning process according to the invention, a cleaning apparatus, and a test apparatus for testing filters and/or containers.

2. Description of the Related Art

From document DE 101 36 785 A1 there is known a cleaning process for a filter test apparatus, in which the filter test apparatus is filled with a cleaning fluid. After a predetermined residence time, the contaminated cleaning fluid is flushed out of the filter test apparatus by means of fresh cleaning fluid.

Starting from the known prior art, it is an object of the invention to achieve an improved cleaning result.

This object is solved by the features of the independent claims. Preferred embodiments are the subject of the dependent claims.

SUMMARY OF THE INVENTION

An aspect of the present invention relates to a cleaning process for a test apparatus having switching means, external connections, internal volumes, which can come into contact with a fluid from a filter to be tested or a container to be tested, the cleaning process comprising the following steps:

selecting one or more internal volumes to be cleaned;
cleaning the selected internal volumes with a cleaning fluid by a corresponding switching of the switching means;
at least partially draining the cleaning fluid left in the selected internal volumes after cleaning;
flushing the selected internal volumes with a flushing fluid different from the cleaning fluid.

Advantageously, the process according to the invention leads to an improved cleaning of the internal volumes, particularly from the microbiological point of view. Advantageously, the cleaning fluid, which is contaminated itself during cleaning of the internal volumes, is prevented either from accumulating or remaining in the internal volumes of the test apparatus or from mixing with the subsequently supplied cleaning fluid or flushing fluid. Particularly in the case that the contaminations of the internal volumes contain bacteria or viruses, it is necessary to completely remove both the contaminations and the contaminated cleaning fluid from the internal volumes of the test apparatus before the test apparatus is put into normal operation again. Moreover, the cleaning process according to the invention can be performed more easily and more safely than cleaning processes known so far.

In the cleaning process according to the invention, which is particularly computer-assisted or computer-controlled, the internal volumes to be cleaned can be selected particularly by switching of the switching means, and particularly all or substantially all internal volumes that can come into contact with a fluid during normal operation of the test apparatus can be cleaned. It is therefore possible to clean internal volumes having been contaminated or soiled by a fluid from an apparatus to be tested. Such an apparatus to be tested can be a filter apparatus or a container.

The cleaning fluid can comprise a detergent, such as dilute or concentrated sodium hydroxide solution. Particularly, the cleaning fluid can consist of a NaOH solution (sodium hydroxide solution or caustic soda lye) with a concentration of approx. 0.1 mol to approx. 2 mol, preferably of approx. 0.1 mol. A further preferred cleaning fluid is a $H_2O_2$ solution from approx. 0.33% to approx. 1%, preferably of approx. 1.0% (hydrogen peroxide solution). Preferably, the cleaning fluid can comprise a solvent, particularly an alcoholic solution or a surfactant solution. The term "fluid" as defined by the present application comprises a liquid phase, a gaseous phase, as well as a mixture thereof. Preferably, approx. 5 to 30 liters of cleaning fluid, further preferably approx. 6 liters, are required to clean the internal volumes.

The partial drainage of the cleaning fluid is performed by a corresponding switching of the switching means, wherein the cleaning fluid is removed from the internal volumes of the test apparatus at least partially, preferably substantially completely. A substantially complete drainage of the cleaning fluid means that the quantity of cleaning fluid remaining in the internal volumes is preferably smaller than approx. 5%, further preferably smaller than approx. 2%, particularly smaller than approx. 1% of the internal volumes of the test apparatus to be cleaned. The drainage is preferably performed in a successive manner, i.e. after the cleaning fluid has remained for a predetermined residence time after the filling of the internal volumes. The residence time may be more than approx. 10 minutes, preferably more than approx. 20 minutes, particularly approx. 60 minutes. Thus, the supplied cleaning fluid can take effect in the internal volumes to be cleaned. The contaminations can be soaked or partially dissolved to remove them from the wall surface of the internal volumes to be cleaned. The drainage may start after the residence time has expired.

Flushing of the selected internal volumes with the flushing fluid advantageously causes the remaining quantity of cleaning fluid to be diluted by the flushing fluid and to be substantially completely flushed or carried out of the internal volumes. The flushing fluid is different from the cleaning fluid. The flushing fluid preferably consists of demineralized, preferably sterile water or ultrapure water. Flushing can be performed with a predetermined flushing time of approx. 10 to 50 minutes. Preferably, approx. 5 to 30 liters of flushing fluid are required to flush the internal volumes.

Preferably, cleaning with the cleaning fluid, draining and/or flushing with the flushing fluid are substantially performed successively. By successively cleaning, draining and/or flushing the internal volumes to be cleaned, a comprehensive cleaning of the internal volumes to be cleaned can be ensured. Moreover, by successively draining and/or flushing the cleaning fluid off the internal volumes, it can be safely ensured that substantially no cleaning fluid is left in the respective internal volume afterwards. Particularly if harmful and/or irritant and/or corrosive cleaning fluids are used, it can be advantageously ensured that residues of the cleaning fluid do not inadvertently contaminate one of the filters or containers to be tested when the test apparatus is used.

Preferably, the cleaning process comprises a further step of at least partially draining the flushing fluid left in the flushed internal volumes after flushing.

For the selection of the internal volumes to be cleaned, drained or flushed, the cleaning process preferably comprises at least one step of pneumatically and/or electrically switching the switching means.

Preferably, the step of draining the flushing fluid off the cleaned and flushed internal volumes is performed substantially successively by correspondingly switching the switching means. Preferably, the step of draining the flushing fluid and drying the internal volumes is performed by means of sterile compressed air or by means of a pressurized gas, particularly of an inert gas, with a pressure of greater than 100 kPa (1 bar), further preferably with a pressure of greater than 200 kPa (2 bar), most preferably 200 kPa (2 bar).

By drying the cleaned and flushed internal volume (preferably with compressed air), it is ensured that substantially no cleaning fluid and/or flushing fluid is left in the cleaned internal volumes.

Preferably, the cleaning process comprises the step of:
cleaning the selected internal volumes by having a vaporous or gaseous cleaning fluid flow through the selected internal volumes by a corresponding switching of the switching means.

Particularly preferably, the cleaning fluid in this case comprises hot steam having a temperature of greater than approx. 121° C., preferably greater than approx. 134° C. Advantageously, the selected internal volumes can be sterilized by this step. Further preferably, the step of sterilizing using hot steam is performed after the flushing fluid has been drained off the internal volumes or after the selected internal volumes have substantially fallen dry. Further preferably, the sterilization with the vaporous or gaseous cleaning fluid can be followed by drainage of the cleaning fluid, particularly by means of a sterile gas, for example sterile compressed air.

An aspect of the present invention relates to a particularly computer-assisted or computer-controlled cleaning process for a test apparatus having switching means, external connections, internal volumes, which can come into contact with a fluid from an apparatus to be tested, the cleaning process comprising the following steps:

selecting one or more internal volumes to be cleaned;
cleaning the selected internal volumes by having a vaporous or gaseous cleaning fluid flow through the selected internal volumes by a corresponding switching of the switching means;
draining the cleaning fluid left in the selected internal volumes after cleaning.

The cleaning fluid may be vaporous or gaseous. To prevent the cleaning fluid from condensing within the internal volumes, the flow of the cleaning fluid through the selected internal volumes is enabled by a corresponding switching of the switching means. Accordingly, a supply of cleaning fluid into and drainage of the cleaning fluid off the selected internal volumes take place at the same time. Advantageously, if a vaporous or gaseous cleaning fluid is used, the quantity of the cleaning fluid left in the internal volumes is limited to the proportion of cleaning fluid condensed in the internal volumes. Further advantageously, no flushing of the internal volumes by means of a flushing fluid is necessary for a low degree of condensation. For example, ozone may be used as a gaseous cleaning fluid, which allows safely killing microbiological organisms and substantially does not accumulate or remain within the internal volumes of the test apparatus. Preferably, draining of the cleaning fluid off the internal volumes can be followed by flushing, preferably with a flushing fluid different from the cleaning fluid. If a vaporous or gaseous cleaning fluid is used, flushing can also be performed with the liquid phase of the cleaning fluid as the flushing fluid.

Preferably, the cleaning fluid is a hot steam having a temperature of greater than approx. 121° C., preferably greater than approx. 134° C. Due to the preferred use of hot water vapor, the hot steam has a positive pressure of approx. 100 kPa (approx. 1 bar) and a positive pressure of approx. 200 kPa (approx. 2 bar) at a temperature of approx. 121° C. and a temperature of approx. 134° C., respectively.

Further preferably, the hot steam is generated from demineralized water. Advantageously, the cleaning fluid condenses to pure water within the selected internal volumes, so that flushing with a flushing fluid is usually not required.

Preferably, however, flushing with a flushing fluid, for example demineralized water, can be performed. According to the invention, hot steam and water are considered to be mutually different fluids. To also achieve a sterilization of the internal volumes in addition to the cleaning, the hot steam is preferably supplied such that the temperature within the internal volumes is at least 121° C. at any point. In order to monitor that this temperature is maintained, a temperature sensor is preferably provided at a point of the internal volumes which has the substantially greatest heat absorption capacity and thus probably the lowest temperature during cleaning with hot steam. This point can preferably be in the region of a cleaning fluid outlet. Further preferably, particularly for configurations of the internal volumes in which the cleaning fluid outlet is not the coldest point within the internal volumes, for example if the outlet is arranged close to the inlet and the inlet temperature is quickly reached by heat conduction at the outlet, the temperature sensor can preferably be arranged in difficult-to-access regions in or at which fluid has accumulated, as the case may be.

Preferably, the step of draining the cleaning fluid and/or the flushing fluid comprises a step of at least partially drying the cleaned and/or flushed internal volumes. Draining can be performed by a corresponding switching of the switching means.

Preferably, the step of drying is performed using compressed air, preferably using sterile compressed air. Preferably, the compressed air has a positive pressure of at least approx. 100 kPa (1 bar) with respect to the atmospheric pressure, further preferably a pressure of greater than 200 kPa (2 bar), particularly preferably 200 kPa (2 bar). The step of drying of the cleaned or flushed internal volumes is performed preferably substantially successively by a corresponding switching of the switching means. By drying of the cleaned or flushed internal volumes, it is ensured that substantially no cleaning fluid or no flushing fluid is left in the cleaned or flushed internal volumes.

Preferably, the cleaning process further comprises the steps of:
collecting the cleaning fluid and/or flushing fluid exiting the selected internal volumes;
separating the collected cleaning fluid and/or the flushing fluid into a liquid phase and a gaseous phase, wherein the liquid phase is collected in an receiving container, and the gaseous phase escapes into the environment.

Collecting of the cleaning fluid and/or flushing fluid exiting the test apparatus during cleaning and/or draining is preferably performed by means of at least one fluid discharge line, which guides the exiting fluids to a collecting apparatus. The collecting apparatus can comprise a collecting container, in which the exiting and optionally contaminated fluids are collected. The collecting container is preferably formed as a so-called "sterile receiver", so that a sterile fluidic connection between the test apparatus, the cleaning apparatus, and the collecting container can be established. Due to the quantity of the required cleaning fluid or flushing fluid, the collecting container preferably has a volumetric capacity of more than approx. 10 liters, further preferably of more than approx. 20 liters, and particularly of more than approx. 60 liters. Preferably, the collecting container has at least one check valve, which prevents fluids from escaping from the collecting container toward the test apparatus or into the environment through the connected at least one fluid discharge line. If a vaporous or gaseous cleaning fluid or flushing fluid is used, the fluid supplied to the collecting apparatus is separated into a liquid phase and a gaseous phase, usually by condensation e.g. on a cooling element, a cooling coil, etc. The gaseous phase can escape into the environment via a valve, for example a pressure relief valve or a check valve.

Preferably, the gaseous phase escapes via a bacteria-retaining apparatus and/or via a virus-retaining apparatus. Particularly if the internal volumes of the test apparatus are contaminated with pathogenic germs and thus the cleaning fluid and/or the flushing fluid might contain pathogenic germs as well, the bacteria-retaining apparatus and/or the virus-retaining apparatus prevents these germs from escaping or exiting into the environment.

Preferably, the cleaning process comprises the step of logging the course of the cleaning process, for example by storage on a data carrier, by generating a printout of a cleaning protocol, or by transmitting the cleaning protocol over a data line.

Computer Program Product

An aspect of the present invention relates to a computer program product, particularly embodied as a signal and/or as a data stream, comprising computer-readable instructions, wherein the instructions perform a process according to the invention when loaded and executed on a suitable computer system. In other words, a computer program product is provided which comprises program parts for performing the process according to the invention or a preferred embodiment thereof. Further, a computer program is provided which, when loaded on a computer, can perform the process according to the invention or a preferred embodiment thereof. Further, a computer-readable storage medium is provided on which such a computer program is stored.

Cleaning Apparatus

An aspect of the present invention relates to a cleaning apparatus for a test apparatus, comprising:
  at least one fluid connection for a container for a cleaning fluid, wherein the fluid connection is fluidically coupled with a complementary or mating connection via a fluid supply line, wherein the complementary connection can be fluidically coupled with an external connection of the test apparatus, and
  at least one fluid connection for a container for a flushing fluid, wherein the fluid connection is fluidically connected with the complementary connection via a fluid supply line;
  at least one apparatus for delivering a cleaning fluid and/or a flushing fluid from one of the containers to the complementary connection; and
  at least one connection for a collecting apparatus for collecting the cleaning fluid and/or flushing fluid exiting the test apparatus, wherein the collecting apparatus can be coupled with at least one external connection of the test apparatus by means of at least one fluid discharge line.

Advantageously, the cleaning apparatus can be handled more easily and safely and achieves an improved cleaning of the test apparatus. The cleaning apparatus comprises at least one fluid connection, preferably two fluid connections, for a cleaning fluid container and a flushing fluid container. It is understood that in addition to or instead of the fluid connections for the containers, the cleaning apparatus can also comprise the containers themselves. The corresponding fluid connections would then be internal fluid connections, which fluidically couple the cleaning fluid container and the flushing fluid container with the associated fluid supply lines. The fluid supply line is fluidically connected with the complementary connection, which can preferably be formed as a complementary plug-in nipple or a complementary plug-in coupling, which can be fluidically connected with an associated plug-in coupling or an associated plug-in nipple of one of the external connections of the test apparatus. It is understood that for practical purposes, a cleaning fluid container and a flushing fluid container are connected with an associated fluid connection at the beginning of the cleaning process to advantageously perform the entire cleaning process without decoupling or coupling fluid lines or fluid connections. However, merely a single fluid connection can be provided, which sequentially serves as a fluid connection for the cleaning fluid container and then as a fluid connection for the flushing fluid container, wherein while the cleaning process is performed, the cleaning fluid container has to be separated from the fluid connection to subsequently connect the flushing fluid container thereto.

The at least one apparatus for delivering the cleaning fluid and/or the flushing fluid is preferably designed or configured such as to deliver both the cleaning fluid and the flushing fluid from the corresponding container to the complementary connection of the cleaning apparatus and further via the external connection coupled therewith into the internal volumes of the test apparatus to be cleaned. Preferably, two delivering apparatuses can be provided, wherein the first delivering apparatus is designed to deliver the cleaning fluid, and the second delivering apparatus is designed to deliver the flushing fluid. The at least one delivering apparatus can be configured as a pump, particularly as a flexible-tube pump.

The cleaning apparatus comprises at least one connection for a collecting apparatus, or preferably the collecting apparatus itself, wherein the connection for the collecting apparatus then is an internal connection of the cleaning apparatus. The collecting apparatus can comprise a collecting container for collecting the cleaning fluid or flushing fluid exiting the test apparatus, wherein the collecting apparatus or the collecting container is coupled with an external connection or multiple external connections of the test apparatus via one or more fluid discharge line(s) during normal operation.

Preferably, the cleaning apparatus comprises at least one switching means controlling the fluid flow through one of the fluid supply lines and/or controlling the fluid flow through one of the at least one fluid discharge lines. Further preferably, the switching means comprise pneumatic switching means and/or electromagnetic switching means. For example, the switching means can be configured as valves, i.e. switching valves or proportional valves, which can be actuated electrically, electromagnetically and/or pneumatically. Preferably, the valves used, e.g. bellows or diaphragm valves, have a small valve volume of preferably less than approx. 10 ml, particularly of less than approx. 1 ml. Particularly, the switching means can be computer-controlled, so that the switching operations for initiating different steps of the cleaning process are advantageously performed automatically, i.e. without any user action or user interaction.

Preferably, the apparatus for delivering the cleaning fluid and/or the flushing fluid can be operated with compressed air or pressurized gas. Particularly, the delivery is performed by pressurizing the container for cleaning fluid or the container for flushing fluid. Due to the positive pressure in the container(s), the fluid contained therein can be delivered via a rising pipe.

An aspect of the present invention relates to a cleaning apparatus for a test apparatus, comprising:
  an apparatus for providing a vaporous or gaseous cleaning fluid, which can be coupled with an external connection of the test apparatus by means of a cleaning fluid supply line;
  at least one connection for a separating apparatus for separating the cleaning fluid exiting the test apparatus into a liquid phase and a gaseous phase, wherein the separating apparatus can be coupled with at least one external connection of the test apparatus by means of a fluid discharge line, and wherein the liquid phase arising in the separating apparatus is collectable in a collecting container, and the gaseous phase arising in the separating apparatus escapes into the environment.

The apparatus for providing a vaporous or gaseous cleaning fluid can preferably comprise an apparatus for producing the vaporous or gaseous cleaning fluid. Moreover, alternatively or in addition to the connection for the separating apparatus, the cleaning apparatus can also comprise the separating apparatus itself. A preferred separating apparatus is a condensation apparatus, such as a cooling element or a cooling coil. The liquid phase arising in the separating apparatus can be collected in a collecting container. Preferably, the collecting container has at least one check valve, so that no fluids from the collecting container can get back into the test apparatus. The gaseous phase can escape into the environment preferably via a valve, for example a pressure relief valve or a check valve, optionally via a filter, a bacteria-retaining apparatus and/or a virus-retaining apparatus.

Preferably, the apparatus for providing the cleaning fluid comprises a hot steam generator generating a hot steam having a temperature of greater than approx. 121° C. Further preferably, the hot steam is generated from demineralized water. Due to the preferred use of hot water vapor, the hot steam has a positive pressure of approx. 100 kPa (>1 bar) at a temperature of greater than approx. 121° C. At a further preferred temperature of greater than approx. 134° C., the positive pressure is greater than approx. 200 kPa (>2 bar). In order to monitor that the preferred minimum temperature of approx. 120° C. is maintained when sterilizing the internal volumes, preferably at least one temperature sensor and/or at least one pressure sensor is/are provided within the internal volumes. Preferably, at least one of the temperature and/or at least one of the pressure sensors is arranged in the region of a cleaning fluid outlet.

Preferably, the cleaning apparatus comprises a bacteria-retaining apparatus and/or a virus-retaining apparatus, via which the gaseous phase escapes into the environment.

Preferably, the cleaning apparatus comprises an apparatus for providing compressed air, preferably sterile compressed air, wherein the compressed air can be supplied to the compressed air supply connection of the test apparatus via a compressed air supply line connection. The compressed air can be used to deliver fluids within the cleaning apparatus and/or the test apparatus connected therewith. Moreover, at least one external connection of the test apparatus is configured such that a compressed air supply line for drying the cleaned or flushed internal volumes is connectable therewith. Thus, drying of the cleaned internal volumes can be performed with compressed air having a suitable pressure, preferably a positive pressure of greater than approx. 100 kPa (>1 bar), further preferably a pressure of greater than 200 kPa (2 bar), particularly preferably 200 kPa (2 bar). Particularly, the compressed air can be supplied to the test apparatus via a compressed air supply line connection of the cleaning apparatus.

Preferably, the apparatus for providing compressed air is pneumatically coupled with the apparatus for delivering the cleaning fluid and/or the flushing fluid. Further preferably, the apparatus for providing compressed air is coupled with pneumatically actuatable switching means of the cleaning apparatus. Advantageously, an additional delivering apparatus for the cleaning fluid or for the flushing fluid, such as an internal or internal pump, can be omitted. By omitting an external pump, the safety in performing the cleaning process is advantageously increased, since fluid couplings or tubes are prevented from coming off. Particularly if a corrosive cleaning fluid is used, the risk of work accidents can be reduced.

Preferably, the cleaning apparatus comprises a connection device comprising at least two complementary or mating external connections of the cleaning apparatus. The compressed air supply line connection, the complementary connection for supplying the cleaning or the flushing fluid, the at least one fluid discharge connection, and the compressed air connection can be part of a connection device as complementary external connections of the cleaning apparatus, which are configured complementarily to the corresponding external connections of the test apparatus. The connection device can preferably cause the geometric distances of the individual, complementary external connections to remain constant to each other. In other words, the individual, complementary external connections are spatially fixed or fixable with respect to each other. Preferably, the connection device can be arranged on the test apparatus by a displacement movement such that the complementary external connections of the connection device can substantially simultaneously be coupled with the associated external connections of the test apparatus. Advantageously, the required connections can be established more quickly, wherein erroneous coupling of the individual connections is prevented in addition. Further preferably, the work safety during the process is increased, since fluid couplings or tubes are prevented from coming off.

Further preferably, the connection device comprises a connector of the cleaning apparatus, which is configured to be electrically coupled with a mating complementary connector of the test apparatus. Preferably, electrical coupling can be performed by displacing the cleaning apparatus along a connection direction A, particularly by a linear displacement. Particularly, the connector or the connection device can be designed or configured for an interface, for example a RS232 interface, a RS435 interface, a RJ45 interface, and/or a USB interface. Further preferably, the connection device can have a connector for the electric power supply of the cleaning apparatus via the test apparatus. Advantageously, a power supply in the cleaning apparatus can be omitted then.

Test Apparatus

An aspect of the present invention relates to a test apparatus for testing filters and/or containers, comprising:
switching means;
external connections;
internal volumes, which can come into contact with a fluid from a filter or container to be tested;
wherein the switching means themselves and the switching means and the external connections are fluidically coupled via the internal volumes, and
wherein the internal volumes of the test apparatus are arranged such that the internal volumes can be substantially completely drained via one of the external connections, which is arranged at the lowest point with respect to the internal volumes.

Advantageously, the test apparatus can be handled more easily and safely and particularly be cleaned more easily and better. Preferably, the switching means of the test apparatus comprise pneumatic switching means and/or electromagnetic switching means. For example, the switching means can be configured as valves, i.e. switching valves or proportional valves, which can be actuated electrically, electromagnetically and/or pneumatically. Preferably, the valves used, e.g. bellows or diaphragm valves, have a small valve volume of preferably less than approx. 10 ml, particularly of less than approx. 1 ml. Particularly, the switching means can be computer-controlled, so that the switching operations for initiating different steps of the cleaning process are advantageously performed automatically, i.e. without any user action.

At least one external connection is configured such that a cleaning fluid or a flushing fluid can be supplied to the test apparatus thereby in order to clean selected internal volumes. Thus, the cleaning apparatus can be coupled with the test apparatus to be cleaned in an easy and safe manner. Furthermore, at least one external connection is configured such that the supplied cleaning fluid or flushing fluid can be discharged or removed thereby.

Further preferably, at least one of the external connections is configured such that a source of compressed air for drying the cleaned or flushed internal volumes can be coupled therewith. Thus, drying of the cleaned internal volumes can be performed using compressed air.

The internal volumes can comprise coupling lines between the switching means, coupling lines between the switching means and the external connections, volumes in the switching means, preferably an internal reference tank, and coupling lines between the internal reference tank and at least one switching means or at least one external connection. Preferably, the internal volumes are defined from parts and/or lines comprising walls of stainless steel and/or Teflon.

Particularly, the switching means, the coupling lines, and the external connections, which define the internal volumes, can be drained substantially completely. Particularly, in normal operation, the coupling lines are sloped with respect to the horizontal defined by the field of gravity of the earth, preferably at an angle of greater than approx. 1 degree, further preferably greater than approx. 5 degrees.

One of the external connections is arranged at the lowest point with respect to the internal volumes during normal operation of the test apparatus to enable a substantially complete drainage of the internal volumes via this external connection.

Preferably, the internal volumes are arranged such that the path from the lowest point of the internal volumes to an arbitrary further point within the internal volumes increases steadily opposite to the direction of gravity in parts, or has a constant height with respect to the direction of gravity at least in parts.

Preferred embodiments of the present invention will be explained in the following by way of example on the basis of the accompanying drawings. Individual features of the illustrated preferred embodiments can be combined to further preferred embodiments.

BRIEF DESCRIPTION OF THE DRAWINGS

FIG. 6 a flow diagram of a preferred cleaning process.

DETAILED DESCRIPTION OF THE PREFERRED EMBODIMENTS

Figure 1:
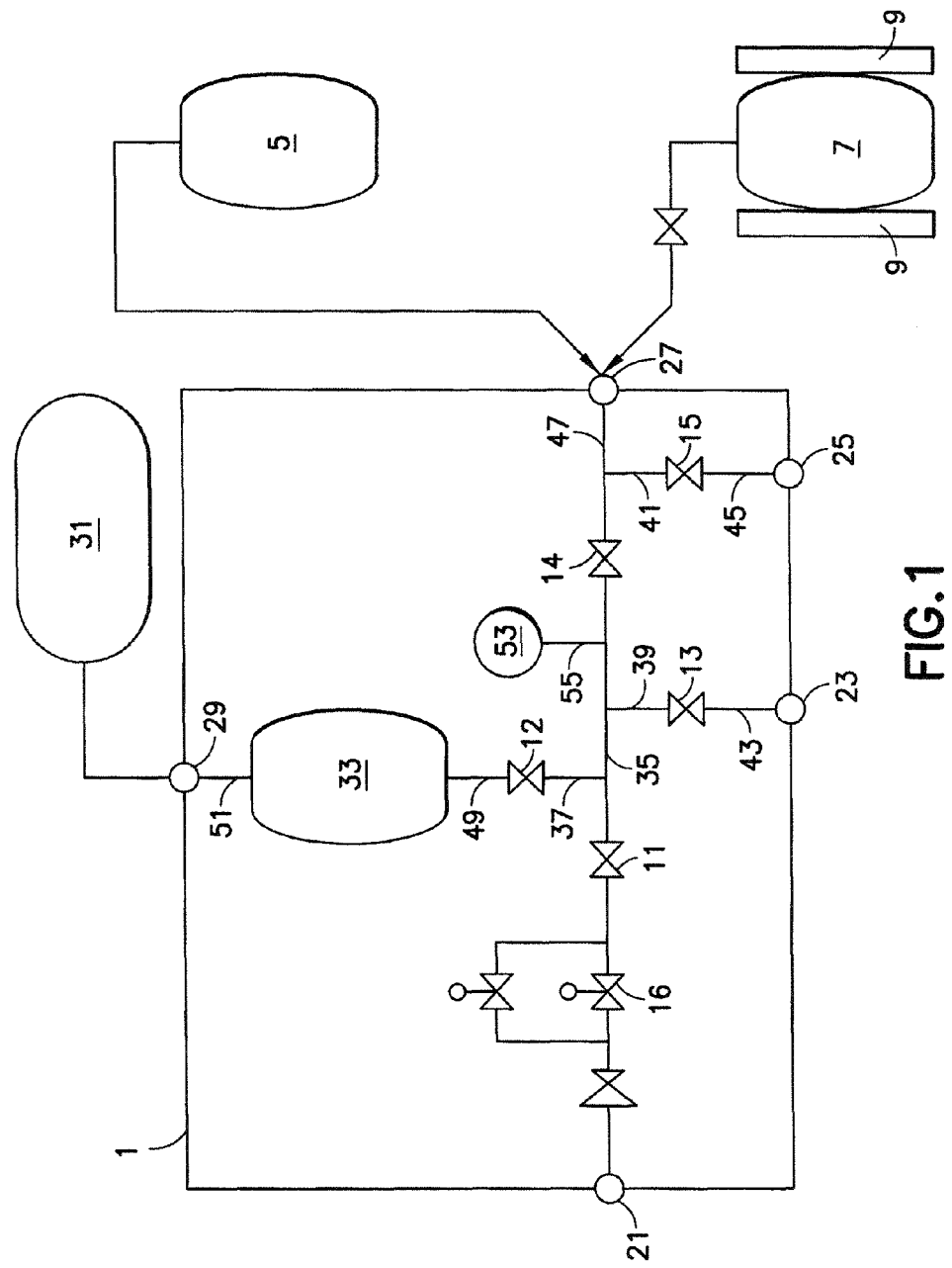
FIG. 1 a schematic structure of a preferred embodiment of a test apparatus for testing filters and/or sterile disposable containers.

FIG. 1 shows a schematic structure of a preferred embodiment of a test apparatus 1 for testing filters 5 or for testing the pressure tightness of containers 7, particularly sterile disposable containers.

The test apparatus 1 comprises valves 11, 12, 13, 14, 15, which are particularly designed as switching valves, and at least one proportional valve 16. Furthermore, the test apparatus 1 comprises external connections 21, 23, 25, 27, 29, wherein the external connections comprise a compressed air supply connection 21, through which compressed air is supplied during the test operation, a connection 23 for internal ventilation, a connection 25 for external ventilation, a test connection 27 for connection of an apparatus to be tested, for example a filter 5 to be tested or a filter apparatus to be tested or a container 7 to be tested, and a connection 29 for an external reference tank 31. Preferably, an internal reference tank 33 is provided in the test apparatus 1. The valves 11, 12, 13, 14, 15 are fluidically coupled with each other via coupling lines 35, 37, 39, 41, i.e. a fluid can flow from one of the switching valves 11, 12, 13, 14, 15 to another one through the coupling lines 35, 37, 39, 41. Furthermore, the valves 11, 12, 13, 14, 15 are fluidically coupled with the respective mating external connections 23, 25, 27 via coupling lines 43, 47, 45. The internal reference tank 33 is coupled with the valve 12 via a coupling line 49, and hydraulically coupled or fluidically coupled with the connection 29 for the external reference tank 31 via a coupling line 51. Furthermore, the test apparatus 1 preferably comprises a pressure gauge 53, which is hydraulically coupled or fluidically coupled with the coupling line 35 via a coupling line 55.

The valves 11, 12, 13, 14, 15 are preferably bellows or diaphragm valves and preferably have a small valve volume $V_{11}$, $V_{12}$, $V_{13}$, $V_{14}$, $V_{15}$, for example a valve volume of less than approx. 5 ml, preferably of less than approx. 1 ml.

The coupling lines 35, 49, 51, 43, 47, 45, 37, 39, 41, 55, the internal reference tank 33, and the internal volumes $V_{11}$, $V_{12}$, $V_{13}$, $V_{14}$, $V_{15}$ of the valves 11, 12, 13, 14, 15 will be referred to as internal volumes in the following. Furthermore, the following exemplary description of a preferred embodiment of the present invention is made with respect to a test apparatus 1 comprising only one proportional valve 16.

During the testing of for example a filter 5, e.g. a membrane filter, the internal reference tank 33 is filled with compressed air having a predetermined or predeterminable pressure. This may be done via the external reference tank 31 or via the compressed air supply connection 21 and the proportional valve 16. During a subsequent measurement, it is determined by means of the reference tank 33 and the pressure gauge 53 how large the pressure drop in the filter 5 is. Since the pressure drop depends on the degree of clogging of the continuous filter membrane pore space, the quality of the filter 5 can thus be determined. In the same or similar way, the pressure tightness of containers 7, particularly sterile disposable containers 7 and sterile flexible bags 7, can be tested. To this end, for example a flexible sterile disposable bag 7 can be arranged between two holding elements 9, which allow the inflation of the disposable bag 7 due to pressurization only to a predetermined or predeterminable volume. If the detected pressure drop after the inflation of the disposable bag 7 is below a predetermined or predeterminable threshold value, the disposable bag is sufficiently tight or is considered to be sufficiently tight.

As part of the test, the filter 5 to be tested or the filter device to be tested or the container 7 to be tested preferably is to be validated as well, i.e. the quality of the filter 5 is to be determined on the basis of predetermined or predeterminable standards. To this end, the test apparatus 1 is preferably connected to the soiled side of the filter 5, i.e. the side to which a fluid to be filtered is supplied during normal operation. However, during the test it may happen that the unfiltered and thus soiled fluid enters the test apparatus 1, in particular its internal volumes, due to a backflow. However, for a validatable testing, it is necessary to ensure that the test apparatus 1 is not contaminated, e.g. with bacteria, viruses, and other contaminations, before each new test process. It is thus required to thoroughly clean the test apparatus 1 preferably before each test process. To further allow an even safer cleaning, the internal volumes are preferably defined by parts or lines that are substantially completely made of stainless steel or a FDA-conform material (FDA: US Food and Drug Administration), for example Teflon.

Furthermore, to prevent fluid from remaining in the internal volumes of the test apparatus 1 or to keep it as little as possible, the internal volumes are preferably arranged according to a hygienic design.

The term "hygienic design" means that the test apparatus can be kept substantially free from vegetative microorganisms, wherein it can be defined thereby that the microbiological failure rate remains within predetermined or predeterminable limits. A predominant pathogen may be Aspergillus niger, a mold fungus, which is capable of decomposing all organic materials and even glass. Aspergillus niger is often used in the food industry to produce citric acid. The fungus tolerates pH ranges from 1.5 to 9.8 and is thus capable of existing both in strongly acidic and alkaline milieus. The cleaning process, the cleaning apparatus and/or the test apparatus are preferably designed such that a contamination with this predominant pathogen is substantially completely removed.

In other words, the internal volumes are arranged such that a substantially complete drainage of the internal volumes is possible via one of the external connections 23, 25, 27, 29. To this end, preferably one of the external connections 23, 25, 27, 29 is arranged such that it is located at the lowest point with respect to the internal volumes during normal operation of the test apparatus 1. Moreover, preferably all further internal volumes are arranged such that the path from the lowest point of the internal volumes to an arbitrary further point within the internal volumes rises steadily in parts opposite to the direction of gravity or has at least a constant height in parts opposite to the direction of gravity. Thus, it is ensured that fluid-filled internal volumes can be drained via an external connection 23, 25, 27, 29 due to the effect of gravity on the fluid.

Further preferably, the internal volumes can be drained by means of compressed air or by means of gas with excess pressure (particularly inert gas), which is provided at the compressed air supply connection 21. Particularly preferably, the drainage in the embodiment shown in FIG. 1 can then be performed via the test connection 27. To ensure a substantially complete drainage of the internal volumes in this case, the dead volumes, i.e. the internal volumes, which are substantially not flown through by compressed air over the path from the compressed air supply connection 21 to the test connection 27, are minimized, particularly preferably zero. In particular, the dead volume of the coupling line 37 is minimized, particularly substantially zero. The term substantially zero particularly means that the line length of the coupling line 37 between the valve 12 and the coupling line 35 is smaller or shorter than the diameter of the coupling line 37, particularly smaller than approx. 1 mm. Thereby, it is advantageously prevented that fluid remains in the coupling line 37 during draining of the internal volumes, for example due to capillary forces. Preferably, the dead volume of the coupling line 55 between the pressure gauge 53 and the coupling line 35 is also substantially zero.

The drainage of the internal volumes can alternatively or in addition be performed via the connection 29 for an external reference tank. Advantageously, the connection 29 can represent the highest point in the fluidically interconnected system of the internal volumes as a rule.

Figure 2:
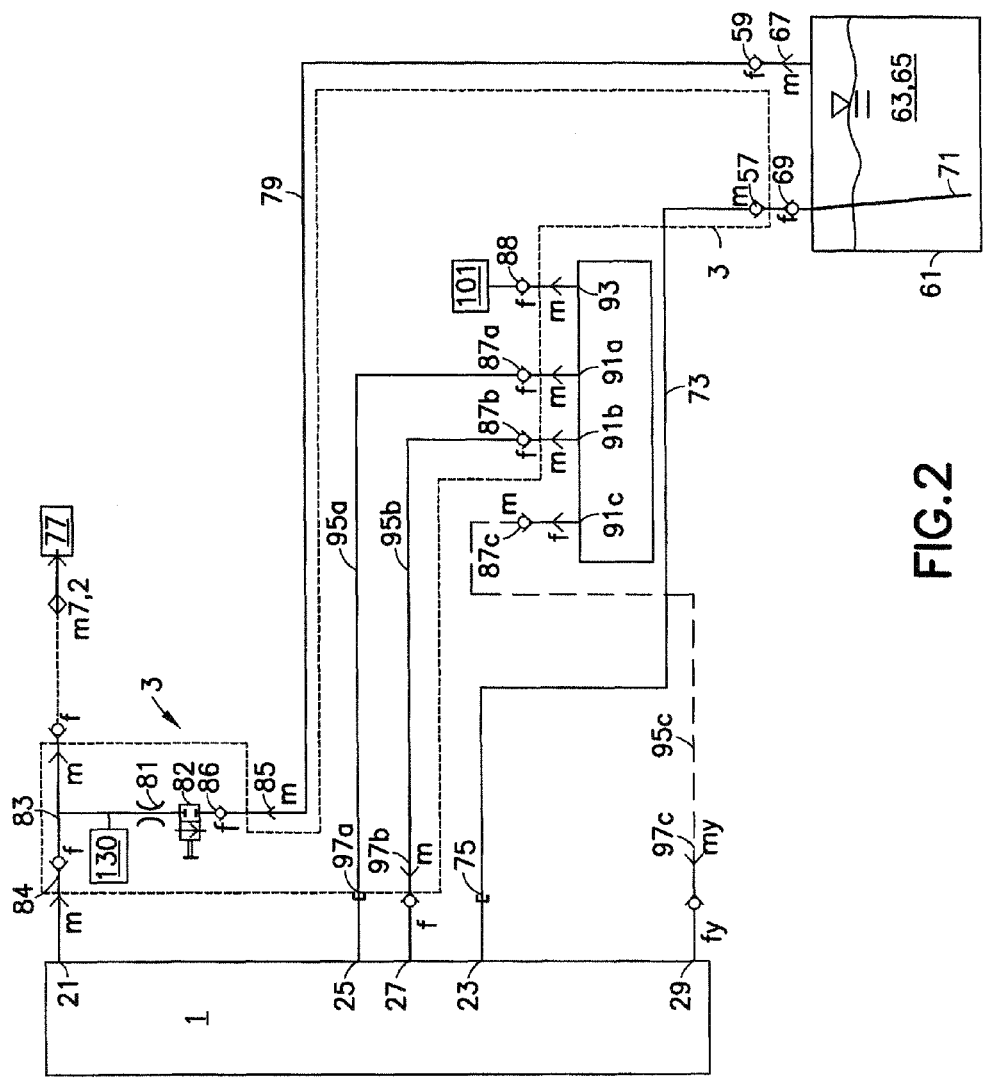
FIG. 2 a schematic structure of a preferred embodiment of a cleaning apparatus for a test apparatus for testing filters and/or sterile disposable containers.

FIG. 2 shows the schematic structure of a preferred embodiment of a cleaning apparatus 3 for a test apparatus 1 for testing filters and/or sterile disposable containers. The cleaning apparatus 3 can comprise a fluid connection 57 and preferably a compressed air connection 59 for a pressure container 61, wherein the pressure container 61 contains a cleaning fluid 63 or a flushing fluid 65 during normal operation. Preferably, as is shown in FIG. 2, the fluid connection 57 or the compressed air connection 59 may also be connections of external lines located outside a preferred housing 4 of the cleaning apparatus 3. The pressure container 61 comprises a compressed air intake 67, which can be coupled with the compressed air connection 59, and a fluid exit 69, which can be coupled with the fluid connection 57, wherein a riser tube 71 is fluidically coupled with the fluid exit 69. The riser tube 71 preferably extends down to the bottom of the pressure container 61. If the pressure container 61 is fed with compressed air via the compressed air intake 67, excess pressure builds up within the pressure container 61, due to which the cleaning fluid 63 or flushing fluid 65 contained in the pressure container 61 rises within the riser tube to escape from the pressure container 61 through the fluid exit 69.

For the normal operation of the cleaning apparatus 3, the fluid exit 69 of the pressure container 61 can be fluidically coupled with one of the external connections 23, 25, 27, 29 of the test apparatus 1 via the fluid connection 57 and a fluid supply line 73, wherein the connection can preferably be established by means of a complementary connection 75, for example by means of a plug-in nipple or a plug-in coupling. The fluid supply line 73 can be formed as an external line. Alternatively, the fluid connection 57 and the complementary connection 75 can be arranged or formed on or in the housing 4 of the cleaning apparatus 3, so that the fluid supply line 73 is arranged within the housing 4 of the cleaning apparatus 3. Preferably, the cleaning apparatus 3 has a temperature and/or a pressure sensor (not shown), which is/are thermally and/or fluidically coupled with the external connection 23, 25, 27, 29 of the test apparatus 1 in order to detect the temperature and/or the pressure of the supplied cleaning fluid 63. Particularly, the pressure sensor can be fluidically coupled with the fluid supply line 73, wherein the fluid supply line 73 is preferably arranged within the housing 4 of the cleaning apparatus 3. In order to supply compressed air to the pressure container 61, the compressed air intake 67 of the pressure container 61 can be connected with a compressed air source 77. Preferably, the compressed air intake 67 of the pressure container 61 is fluidically coupled with the compressed air source 77 via a compressed air supply line 79, a pressure reducer 81, and a compressed air valve 82. As is shown, the compressed air line 79 may be an external line having a compressed air inlet 85, which can be coupled with a compressed air outlet 86 of the pressure valve 82. Alternatively, the compressed air line 79 can be arranged within the housing 4 of the cleaning apparatus 3, wherein then particularly the compressed air connection 59 is also arranged in or on the housing, and particularly the compressed air inlet 85 and the compressed air outlet 86 may be internal connections within the housing 4. Alternatively or in addition to the pressure reducer 81, the pressure reduction can be performed by means of reducing the cross section of the compressed air line 79. Particularly, the compressed air source 77 can be the same compressed air source 77 that provides the compressed air at the compressed air supply connection 21 of the test apparatus 1. Here, a T-connection 83 can be arranged between the compressed air source 77 and the compressed air supply connection 21, so that the compressed air supply connection 21 and the compressed air intake 67 together are fluidically coupled with the pressure source 77. It is understood that both the pressure reducer 81 and the T-connection 83 can be part of the cleaning apparatus 3, i.e. for example can be arranged at least partially in the housing 4 with other components of the cleaning apparatus 3. In this case, the cleaning apparatus 3 preferably has a primary compressed air inlet, which can be fluidically coupled with the compressed air source 77, and a compressed air supply line connection 84, which can be fluidically coupled with the compressed air supply connection 21 of the test apparatus 1. Preferably, the housing 4 of the cleaning apparatus 3 can have a compressed air outlet 86 to which an external compressed air supply connection 79 can be coupled. Alternatively, the pressure reducer 81 and/or the T-connection 83 can be designed as external components, wherein the compressed air is supplied to the compressed air inlet 85 of the cleaning apparatus 3 or the compressed air inlet 85 of the compressed air supply line 79 in a reduced or unreduced form, the inlet being fluidically coupled with the compressed air supply line 79. The compressed air supply connection 21 of the test apparatus 1 can be coupled with a compressed air supply line connection 84 of a compressed air line, which is fluidically coupled with the T-connection 83 or the compressed air outlet of the cleaning apparatus 3. Alternatively, the compressed air supply connection 21 can be coupled with a compressed air supply line connection 84 that is formed as the compressed air outlet of the cleaning apparatus 3. The test apparatus 1 can be supplied with compressed air via the compressed air supply line connection 84. Further preferably, the compressed air source 77 produces a pressure of approx. 500 to approx. 900 kPa (5 to 9 bar), which is applied to the compressed air supply connection 21 of the test apparatus 1. The pressure reducer 81 or the compressed air line 79 is/are preferably designed such that at the compressed air inlet 85 of the cleaning apparatus 3 or the compressed air intake 67 of the pressure container merely a pressure of approx. 100 to approx. 200 kPa (1 to 2 bar), further preferably a pressure of approx. 200 kPa (2 bar), is applied.

Further preferably, the cleaning apparatus 3 comprises a pressure sensor 130, which is preferably fluidically coupled with the T-connection 83 to detect or measure the pressure of the compressed air provided by the compressed air source 77. The pressure sensor 130 can at least partially be arranged within the housing 4 or be formed as an external pressure sensor 130. Advantageously, it can de determined by means of the pressure sensor 130 whether the compressed air source 77 provides the preferred pressure of approx. 500 kPa to approx. 900 kPa. Thereby, the pressure of the compressed air required for a safe operation of the test apparatus 1 and the cleaning apparatus 3 can advantageously be detected and monitored. Further preferably, on the assumption that no pressure drops occur in the pressure container 61 and in the fluid supply line 73, the pressure sensor 130 can also be used to determine the pressure of the fluid supplied to the test apparatus 1.

The cleaning apparatus 3 further comprises at least one connection 87a, 87b, 87c for a collecting container 89, which during normal operation collects the fluids exiting or flowing out of the internal volumes 35, 49, 51, 43, 47, 45, 37, 39, 41, 55, 33, $V_{11}$, $V_{12}$, $V_{13}$, $V_{14}$, $V_{15}$. At least one of the connections 87a, 87b, 87c can preferably be arranged or formed in or on the housing 4 of the cleaning apparatus 3. The collecting container 89 comprises at least one fluid supply 91a, 91b, 91c and a vent 93. For the normal operation of the cleaning apparatus 3, the at least one fluid supply 91a, 91b, 91c of the collecting container 89 can be fluidically coupled with one of the external connections 23, 25, 27, 29 of the test apparatus 1 via at least one fluid discharge line 95a and one fluid discharge connection 97a, wherein the fluid discharge connection 97a is preferably a connection that is complementary to the respective external connection 23, 25, 27, 29, for example a plug-in nipple or a plug-in coupling. It is understood that also a plurality of external connections 23, 25, 27, 29 of the test apparatus 1 can be coupled with an associated fluid supply 91a, 91b, 91c of the collecting container 89 via an associated fluid discharge line 95a, 95b, 95c via fluid discharge connections 97a, 97b, 97c.

To advantageously prevent excess pressure from building up in the collecting container 89, a vent 93 is provided to allow the gaseous phase of the fluid supplied to the collecting container 89 and the air or gas displaced by the fluid in the connecting container to escape into the environment. To prevent the test apparatus 1 from being contaminated by a fluid flowing back from the collecting container 89, the fluid supplies 91a, 91b, 91c are preferably provided with a check valve. Particularly preferably, the fluid supplies 91a, 91b, 91c are formed as plug-in nipples or plug-in couplings, which each have a closure valve and/or a check valve. Alternatively or in addition, a closure valve and/or a check valve can be arranged in a complementary plug-in coupling or a complementary plug-in nipple of the connections 87a, 87b, 87c of the fluid discharge lines 95a, 95b, 95c. Further preferably, a bacteria-retaining apparatus or a virus-retaining apparatus 101 is arranged downstream of the vent 93 to advantageously prevent the environment from being contaminated by pathogenic germs exiting the test apparatus. The bacteria-retaining apparatus or the virus-retaining apparatus 101 can be fluidically coupled with the vent 93 by means of a retaining apparatus connection 88, particularly be fluidically coupled in a sterile manner. Preferably, the bacteria-retaining apparatus or the virus-retaining apparatus 101 is at least partially arranged within the housing 4 of the cleaning apparatus 3, as is shown in FIG. 2, wherein the retaining apparatus connection 88 is preferably arranged or formed in or on the housing 4. Alternatively, the bacteria or virus-retaining apparatus 101 can also be arranged as an external apparatus outside the housing.

Figure 3A:
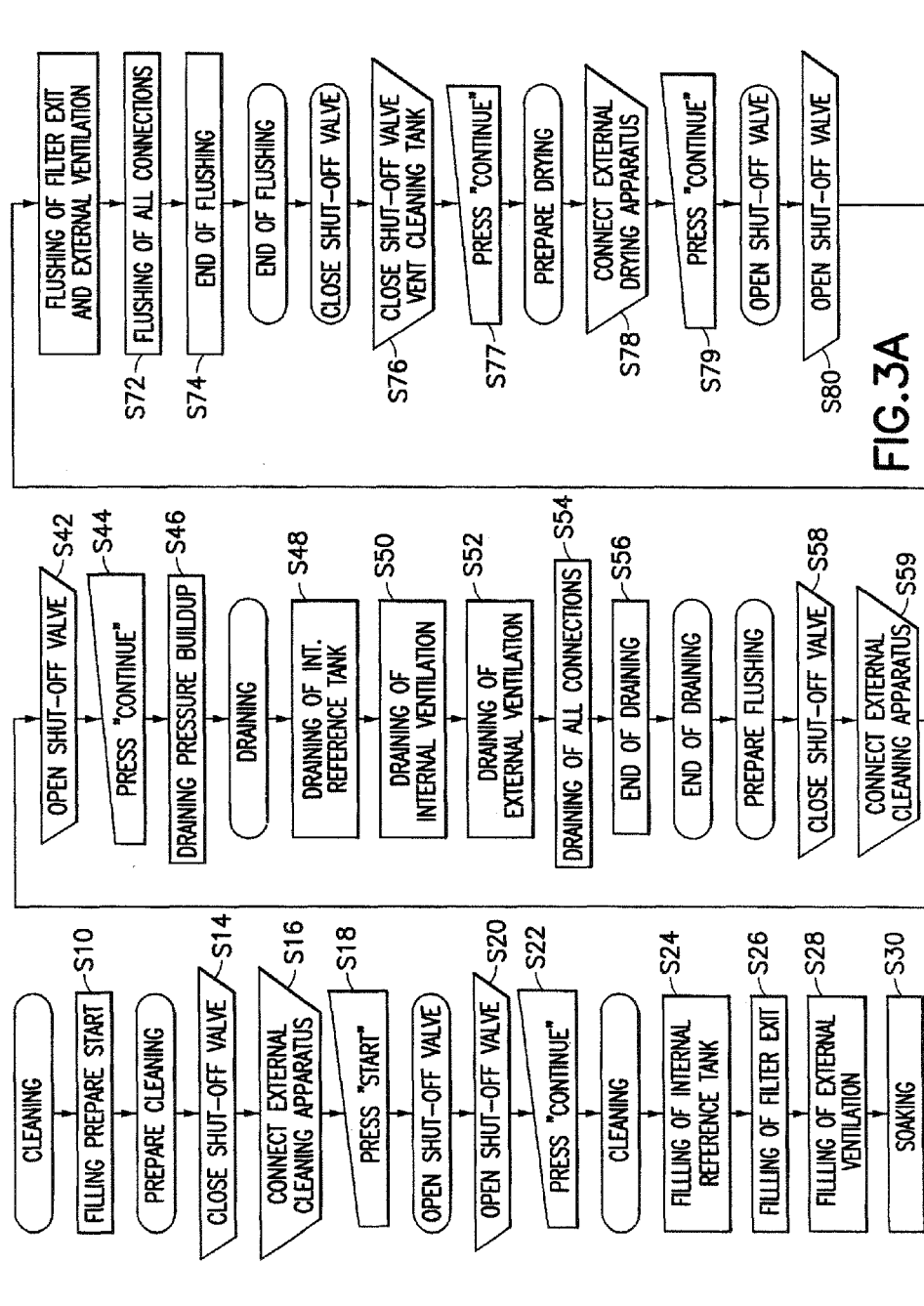
FIG. 3 a flow diagram of a preferred cleaning process.

FIG. 3 shows a flow diagram of a preferred cleaning process with reference to FIGS. 1 and 2. At the beginning of cleaning, the test apparatus 1 is in a normal state, wherein the switching valves 11, 14 and the proportional valve 16 are closed and the switching valves 12, 13, 15 are open. In an initialization step S10, a pressure container 61 is filled with a cleaning fluid 63 and the test apparatus 1 is put into a start state for cleaning, wherein the switching valves 11, 12, 13, 14 and the proportional valve 16 are closed, while the switching valve 15 remains open.

In a subsequent step S14 of the cleaning process, the cleaning apparatus 3 is provided and the compressed air valve 82 of the cleaning apparatus 3 is closed. Subsequently, the compressed air source 77 is coupled with the compressed air supply connection 21 of the test apparatus 1, the complementary connection 75 of the fluid supply line 73 is connected with the external connection 23 of the test apparatus 1, and the fluid discharge lines 95a, 95b, 95c is connected with the external connections 25, 27, 29 via the fluid connections 97a, 97b, 97c of the cleaning apparatus 3 during a process step S16. In a further process step S18, the user is asked to confirm the correct connection of the cleaning apparatus 3 with the test apparatus 1 and to start the cleaning of the test apparatus 1, for example by operating a start button.

After cleaning has been started, the compressed air valve 82 is opened in a step S20, so that compressed air enters the pressure container 61 from the compressed air source 77 via the T-connection 83, the pressure reducer 81, the compressed air valve 82, and the compressed air line 79. Thereby, excess pressure builds up within the pressure container 61, which preferably is approx. 1 to 2 bar, further preferably approx. 2 bar. In a further step S22, preferably after a predetermined or predeterminable operating pressure within the pressure container 61 has been reached, the user is asked to confirm the proper state of the test apparatus 1 and the cleaning apparatus 3. Particularly, the user can check during this step whether a leakage occurred in the cleaning apparatus 3 with excess pressure.

After the confirmation, the actual cleaning process or the actual cleaning steps are performed. In a step S24, the switching valves 12, 13 are opened and the switching valve 15 is closed to fill the internal reference tank 33 with the cleaning fluid 63 from the pressure container 61. In doing so, due to the excess pressure in the pressure container 61, i.e. by pneumatic conveyance, the cleaning fluid 63 rises through the riser pipe 71 via the fluid supply line 73 to the external connection 23 for internal ventilation of the test apparatus 1. Starting from the external connection 23, the cleaning fluid 63 flows to the internal reference tank 33 via the line 43, the switching valve 13, the lines 39, 35, 37, the switching valve 12, and the line 49. From there, the cleaning fluid 63 can flow further via the line 51 and from the external connection out of the test apparatus. Filling of the internal reference tank 33 is preferably determined by means of a predetermined or predeterminable filling time T24.

Subsequently, after the internal reference tank 33 has been filled, filling of the external connection 27, which is adapted for connection of a filter 5 or a container 7, is performed in a step S26. To this end, in step S26, the switching valve 12 is closed and the switching valve 14 is opened, so that the cleaning fluid 63 can flow to the external connection 27 via the line 35, the switching valve 14, and the line 47. Preferably, the filling process is time-controlled and thus terminated after a predeterminable filling time T26. Finally, in a step S28, the remaining part of the internal volumes, i.e. the line 41, the switching valve 15, and the line 45, are filled with the cleaning fluid 63 after the switching valve 15 has been opened. This filling process is also terminated preferably after a predeterminable filling time T28.

Filling of the internal volumes during the cleaning steps S24, S26, and S28 usually causes cleaning fluid 63 to exit the test apparatus 1 via the external connections 25, 27, 29. This exiting cleaning fluid 63 is lead to a collecting container 89 via the fluid discharge lines 95a, 95b, 95c connected to the external connections 25, 27, 29. Preferably, the filling times T24, T26, and T28 are such that cleaning fluid exits from all external connections 25, 27, 29 and flows to the collecting container 89, so that it is advantageously ensured that all internal volumes are filled with cleaning fluid 63.

In a subsequent cleaning step S30, the switching valves 13, 14 are closed and the switching valve 12 is opened. In this state of the test apparatus 1, the cleaning fluid 63 resides within the internal volumes, so that contaminations can be removed from the walls of the internal volumes by soaking or dissolving by means of the cleaning fluid 63. In this state, the test apparatus pauses for a predetermined or predeterminable soaking time T30, which is preferably approx. 10 to approx. 60 minutes.

At the end of the cleaning process, the switching valve 12 is closed in a cleaning step S32. To substantially drain the internal volumes filled with the cleaning fluid 63, the following measures are conducted in a step S34. The compressed air valve 82 of the cleaning apparatus 3 is closed and the connection 85 of the compressed air line 79 is disconnected from the compressed air outlet 86, which is fluidically coupled with the compressed air valve 82. Preferably, this step has to be performed and confirmed by the user. Subsequently, the fluid discharge line 95c at the connection for the collecting container 87c is disconnected from the fluid supply 91c of the collecting container 89, and the fluid discharge line 95c is fluidically coupled with the compressed air outlet 86 by means of the connection 87c. Alternatively, the compressed air supply line 79 at the compressed air connection 59 could be disconnected from the compressed air intake 67 of the pressure container 61 to couple the compressed air connection 59 with the external connection 29 of the test apparatus.

The fluid supply line 73 between the pressure container 61 and the external connection 23 of the test apparatus 1 is disconnected from the fluid exit 69 of the pressure container 61. Instead, the fluid supply line 73 is coupled with the fluid connection 91c of the collecting container 89 by means of the connection 57.

Figure 4:
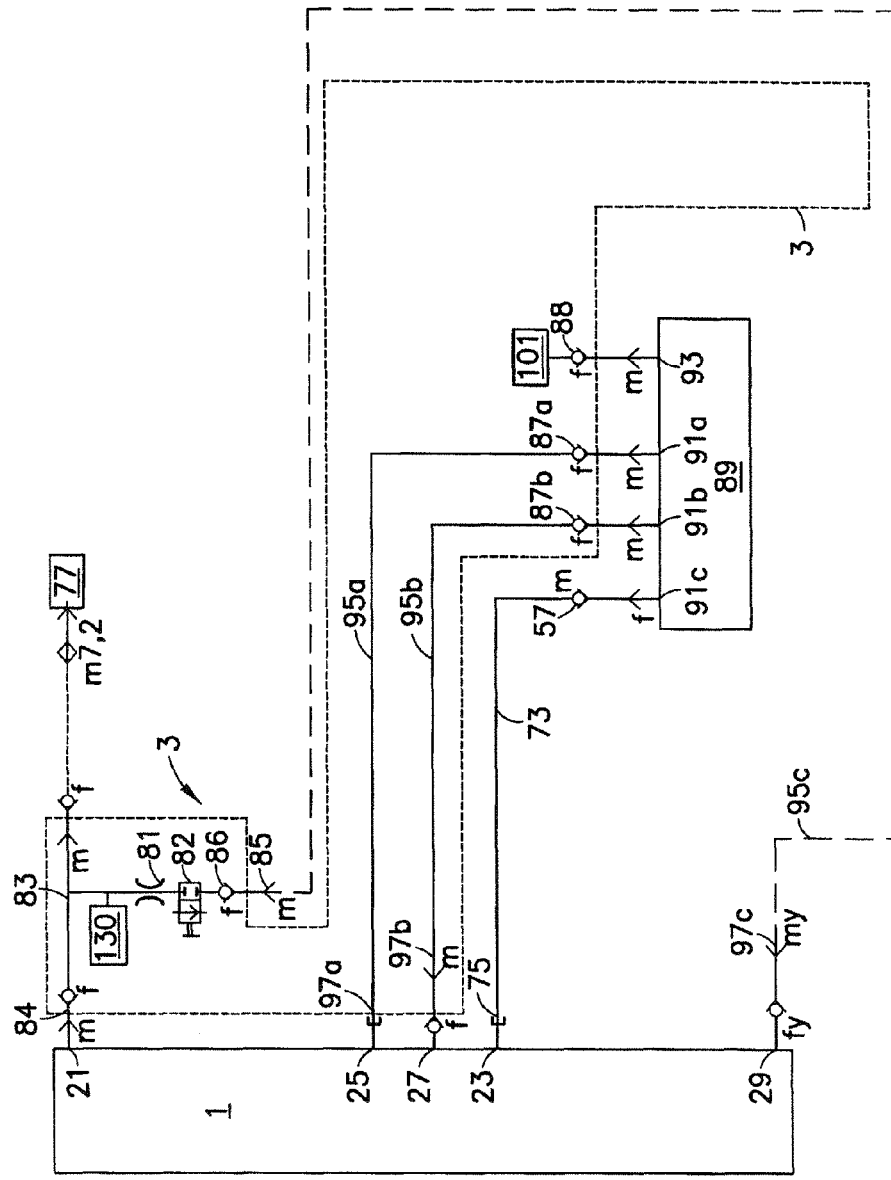
FIG. 4 a schematic structure of the embodiment of the cleaning apparatus during a drying step.

FIG. 4 shows the arrangement of the test apparatus 1 and the cleaning apparatus 3 after step S34 has been performed. The following further description of the cleaning process thus relates to FIG. 4. The proper establishment of all fluid connections is preferably indicated to the system by a user input in a step S40.

To drain the internal volumes, the compressed air valve 82 is opened in a step S42, so that excess pressure builds up at the external connection 29. The proper state of the test apparatus 1 and of the cleaning apparatus 3, in particular the tightness of all connections, is confirmed by the user by a user input in a step S44.

After that, the switching valve 12 is opened in a step S46. By opening the switching valve 12, the excess pressure applied to the external connection 29, which is provided by the compressed air source 77, is applied to the internal volumes 51, 33, 49, V12, 37, 35, 39, 55, so that successive draining of the internal volumes can be started with subsequently. In a step S48, the switching valve 13 is opened to drain the internal reference tank 33 via the external connection 23. The drain time T48 is preferably at least approx. 120 seconds.

To drain the internal volumes V11, 35, 39, V13, 43, the switching valve 12 is closed in a step S50, the switching valve 14 is opened, and the proportional valve 16 is at least partially, preferably approx. 50%, opened. The duration T50 of the pressure buildup is preferably approx. 10 seconds. After that, in the step S50, the switching valve 11 is opened, and the switching valves 13, 14 are alternatingly opened and closed, preferably for a duration of approx. 10 seconds. Further preferably, the overlap time, during which both switching valves 13, 14 are open or closed, is approx. 1 s or more. In this step S50, the cleaning fluid 63 can be drained from the volumes of the lines 35, 39, 43, 41, 45, 47 and the volumes V13, V14, V15 of the switching valves 13, 14, 15 via the external connections 23, 25, 27 into the collecting container 89.

In a subsequent step S52, the switching valves 11, 14, 15 are opened and the switching valves 12, 13 are closed, wherein the proportional valve 16 remains opened preferably approx. 50%. Now, the switching valve 15 is opened and closed in an alternating manner, preferably at intervals of approx. 10 seconds, to drain the internal volumes of the switching valve 15 and the lines 41, 45 via the external connection 25. The lines 47 are drained alternatingly via the connection 27.

Subsequently, in step S54, all switching valves 11, 13, 14, 15 except for the switching valve 12, which separates the internal reference tank 33, and the proportional valve 16 are opened to drain all external connections 23, 25, 27 except for the external connection 29 for the external reference tank 31, which has already been drained via the internal reference tank 33. After a predetermined or predeterminable drain time, all switching valves 11, 12, 13, 14 and the proportional valve 16 are closed, while the switching valve 15, which is associated with the external vent 25, remains open. After the step S56 has been completed, flushing of the internal volumes is prepared.

After the test apparatus 1 has been drained, the flushing of the internal volumes of the test apparatus 1 is prepared in a step S58. To this end, the compressed air valve 82 is closed and the test apparatus 1, the cleaning apparatus 3, and the pressure container 61—as is shown in FIG. 2—are fluidically coupled with each other (step S59). This structure corresponds to the structure shown in FIG. 2, which was used to clean the test apparatus 1 by means of the cleaning fluid 63, wherein instead of the cleaning fluid 63, the pressure container 61 was filled with a flushing fluid 65 different from the cleaning fluid 63, or wherein the pressure container 61 containing the cleaning fluid 63 was exchanged for a pressure container 61 containing the flushing fluid 65.

As soon as the corresponding connections are correctly connected with each other, the proper assembly of the test apparatus 1 with the cleaning apparatus 3 is confirmed by the user (step S60). Subsequently, in a step S62, the compressed air valve 82 is opened. The compressed air valve 82 can be opened automatically or manually, wherein the opening of the compressed air valve 82 is then confirmed by the user in a step S64.

To fill the internal reference tank 33, the switching valves 12, 13 are opened in a step S66. The switching valve 15 is also open, while the switching valves 11, 14 and the proportional valve 16 are closed. After a predetermined flushing time T66, the switching valve 12 is closed and the switching valve 14 is opened to fill the internal volume of the test connection 27 and the coupling line 47 with flushing fluid 65 in a step S68. After a predetermined flushing time T68, the switching valve 15 is opened to fill the internal volumes of the coupling lines 41, 45 and the switching valve 15 with the flushing fluid 65 in a step S70. Preferably, the cleaning steps S66, S68, and S70 can be repeated in an alternating manner. After that, the switching valves 12, 13, 14, 15 are opened to flush all external connections 23, 25, 27, 29 of the test apparatus 1 with the flushing fluid 65 in a step S72. The flushing fluid 65 exiting the test apparatus 1 during the flushing of the internal volumes is lead into the collecting container 89 via the fluid discharge lines 95a, 95b, 95c. At the end of the flushing process, the switching valves 11, 12, 13, 14, and 16 are closed in a step S74. Further, the compressed air valve 82 is closed in a step S76, wherein the closing of the compressed air valve 82 is confirmed by the user in a step S78.

To drain the flushing fluid 65 off the internal volumes of the test apparatus 1 or to dry the internal volumes of the test apparatus 1, the connection 85 of the compressed air line 79 is disconnected from the compressed air outlet 86. Preferably, this step has to be performed and confirmed by the user. Subsequently, the fluid discharge line 95c at the connection for the collecting container 87c is disconnected from the fluid supply 91c, and the fluid discharge line 95c is fluidically coupled with the compressed air outlet 86 by means of the connection 87c. The fluid supply line 73 is removed from the pressure container 61. Instead, the fluid supply line 73 is coupled with the fluid connection 91c of the collecting container 89 by means of the connection 57.

To drain the flushing fluid 65 off the internal volumes of the test apparatus 1 or to dry the internal volumes of the test apparatus 1, the compressed air supply line 79 can be disconnected from the pressure container 61 as an alternative to the above-described procedure, to couple the compressed air supply line 79 with the test apparatus 1, preferably by connecting the compressed air connection 59 with the connection 29 for an external reference tank, wherefore the fluid discharge line 95c has been removed from this connection in advance. The fluid supply line 73 can also be removed, which is coupled with the connection 23 of the test apparatus 1. The fluid discharge line 95c is then coupled with the connection 23.

This results in a structure as is shown in FIG. 4. The proper assembly is confirmed by the user in a step S79.

Subsequently, the compressed air valve 82 is opened in a step S80, and the opening of the compressed air valve 82 is confirmed by the user in a step S82.

In a first step S84 of drying the internal volumes of the test apparatus 1, the switching valves 12, 13 are opened. After a predetermined or predeterminable drying time T84 or preferably approx. 120 seconds, the switching valve 12 is closed to suppress the flow of compressed air through the internal reference tank 33 in a drying step S86. Preferably, the switching valve 12 remains closed for a period of approx. 10 seconds during the drying step S86. Further preferably, the steps S84 and S86 are performed in an alternating manner. Further preferably, the steps S84 and S86 are repeated approx. fifteen times.

Subsequently, in a step S88, the switching valves 11, 12, 14 are closed and the switching valves 13, 15 are opened. Furthermore, the proportional valve 16 is opened at least partially, preferably approx. 50%. Since the switching valve 11 is closed, a pressure is build up via the compressed air supply connection 21 and the proportional valve 16. After that, the switching valve 11 is opened and then, preferably several times, the switching valves 13, 14 are opened and closed in an alternating manner. Preferably, the opening and closing times of the switching valves 13, 14 are approx. 10 seconds. Further preferably, the overlap time during which both switching valves 12, 14 are open or closed at the same time, is approx. 1 s. After a predetermined or predeterminable drying time T80 of preferably approx. 2 minutes, the cleaning step S88 is terminated.

Subsequently, the switching valves 11, 14, 15 are opened and the switching valves 12, 13 are closed. To dry the connection 25 for the external ventilation of the test apparatus 1, the switching valve 15 is alternatingly opened and closed in a step S90, wherein the opening and closing times preferably are approx. 10 seconds. After a predetermined drying time T90, the switching valves 11, 13, 14, 15 are opened and the switching valve 12 is closed to dry all external connections 23, 25, 45, 29 in a step S92. At the end of the drying process, the switching valves 11, 12, 13, 14 and the proportional valve 16 are closed in a step S94. The compressed air valve 82 is also closed. The termination of the cleaning process can preferably be confirmed by a user. Further preferably, the test apparatus can be put into a normal state after cleaning, in which the switching valves 11, 14 and the proportional valve 16 are closed, while the switching valves 12, 13, 15 are open.

It is understood that the actuation of the compressed air valve 82 and the establishment and disconnection of the corresponding required fluid connections between the test apparatus 1, the cleaning apparatus 3, and the pressure container 61 can be performed both manually by a user and automatically by corresponding switching means. Accordingly, the cleaning process can be performed as a computer-assisted cleaning process or as a manual cleaning process.

Preferably, the cleaning process comprises the step of logging the course of the cleaning process, for example by storage on a data carrier, by generating a printout of a cleaning protocol, or by transmitting the cleaning protocol over a data line. Further preferably, the cleaning process comprises the step of determining the predetermined or predeterminable times T24, T26, T28, T30, T48, T50, T66, T68, T80, T84, and T90, particularly by performing a test run.

Figure 5:
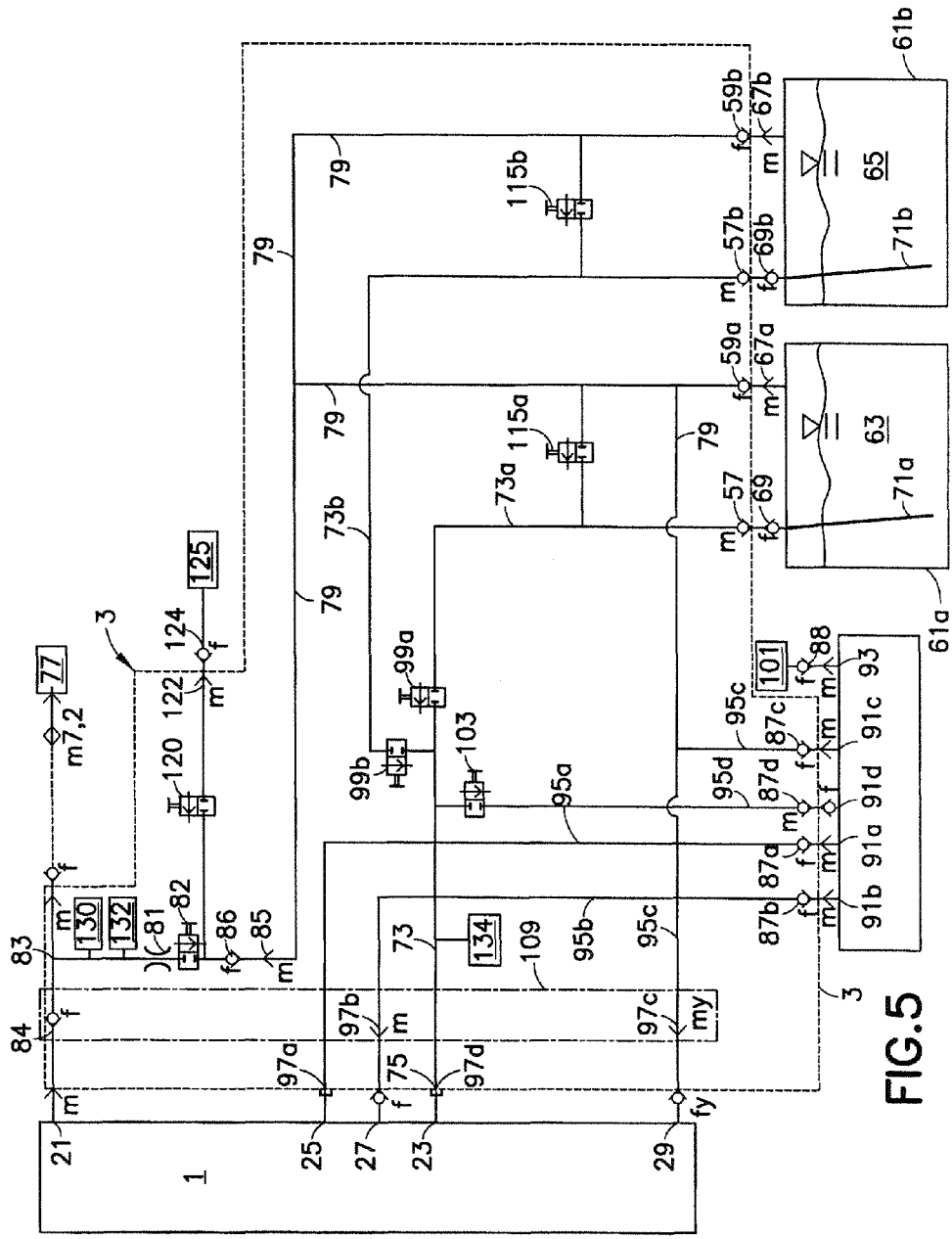
FIG. 5 a schematic structure of a preferred embodiment of a cleaning apparatus for a test apparatus.

FIG. 5 shows the schematic structure of a further preferred embodiment of a cleaning apparatus 3 for a test apparatus 1 for testing filters and/or sterile disposable containers. The cleaning apparatus 3 is adapted to be operated with a first pressure container 61a, which contains a cleaning fluid 63 during normal operation, and with a second pressure container 61b, which contains a flushing fluid 65 during normal operation. To this end, the cleaning apparatus 3 comprises a first fluid connection 57a and a first compressed air connection 59a for the first pressure container 61a, and a second fluid connection 57b and a second compressed air connection 59b for the second pressure container 61b. The compressed air connections 59a, 59b and/or the fluid connections 57a, 57b are preferably formed or arranged in or on a housing 4 of the cleaning apparatus.

The first and second pressure containers 61a, 61b comprise a compressed air intake 67a, 67b, respectively, which can be coupled with the associated compressed air connection 59a, 59b, and first and second fluid exits 69a, 69b, which can be coupled with the associated first or second fluid connection 57a, 57b. Here, riser pipes 71a, 71b are fluidically coupled with the associated fluid exits 69a, 69b, respectively. The riser pipes 71a, 71b preferably extend down to the bottoms of the pressure containers 61a, 61b. If the pressure containers 61a, 61b are fed with compressed air via the compressed air intakes 67a, 67b, excess pressure builds up within the pressure containers 61a, 61b, due to which the cleaning fluid 63 contained in the pressure container 61a or the flushing fluid 65 contained in the pressure container 61b can rise within the riser tubes to escape from the pressure containers 61a, 61b through the fluid exits 69a, 69b.

To supply compressed air to the first and second pressure containers 61a, 61b, the compressed air intakes 67a, 67b of the pressure containers 61a, 61b can be coupled with a compressed air source 77. Preferably, the compressed air intakes 67a, 67b are fluidically coupled with the compressed air source 77 via a common compressed air supply line 79 and compressed air valve 82. The compressed air supply line 79 can comprise a compressed air inlet 85 as well as a first compressed air connection 59a for the first pressure container 61a and a second compressed air connection 59b for the second pressure container 61b. The compressed air valve 82 can be formed as a proportional valve, which is preferably controlled electrically, and can act as a pressure reducer. In particular, the compressed air source 77 can be the same compressed air source 77 that provides the compressed air at the compressed air supply connection 21 of the test apparatus 1. Here, a T-connection 83 can be arranged between the compressed air source 77 and the compressed air supply connection 21, so that the compressed air supply connection 21 and the compressed air intake 67 together are fluidically coupled with the pressure source 77. It is understood that both the compressed air valve 82 and the T-connection 83 can be part of the cleaning apparatus 3, i.e. for example can be arranged at least partially in the housing 4 with other components of the cleaning apparatus 3. In this case, the cleaning apparatus 3 has a compressed air inlet and a compressed air supply line connection 84, which can be fluidically coupled with the compressed air supply connection 21 of the test apparatus 1. Preferably, the cleaning apparatus 3 can have a compressed air outlet 86 to which an external compressed air supply connection 79 can be coupled. Alternatively, the compressed air valve 82 and/or the T-connection 83 can be designed as external components, wherein the compressed air is supplied to the compressed air inlet 85 of the cleaning apparatus 3, which is fluidically coupled with the compressed air supply line 79, in a reduced or unreduced form. Further preferably, the compressed air source produces a pressure of approx. 500 to approx. 900 kPa (5 to 9 bar), which is applied to the compressed air supply connection 21 of the test apparatus 1. The compressed air valve 82 is preferably designed or adjusted such that at the compressed air inlet 85 of the cleaning apparatus 3 or at the compressed air intakes 67a, 67b of the pressure containers 61a, 61b merely a pressure of approx. 100 to approx. 200 kPa (1 to 2 bar), further preferably of approx. 2 bar, is applied.

Further preferably, the cleaning apparatus 3 comprises a pressure sensor 130 and/or a moisture sensor 132, which is/are preferably fluidically coupled with the T-connection 83 to detect or measure the pressure or moisture of the compressed air provided by the compressed air source 77. Both the pressure sensor 130 and the moisture sensor 132 can at least partially be arranged within the housing 4 or be formed or arranged externally. Advantageously, it can de determined by means of the pressure sensor 130 whether the compressed air source 77 provides the preferred pressure of approx. 500 kPa to approx. 900 kPa. Thereby, the pressure of the compressed air required for a safe operation of the test apparatus 1 and the cleaning apparatus 3 can advantageously be detected and monitored. Further preferably, the relative and/or absolute moisture of the provided compressed air can be detected or measured by means of the moisture sensor. Thereby, it can be checked, for example, whether the provided compressed air has a sufficiently low moisture content for drying the internal volumes. Further preferably, at least one further moisture sensor can be provided, which is fluidically coupled with one of the external connections 23, 25, 27 to detect or measure the moisture of the air exiting the internal volumes. Advantageously, the progress or the quality of the drying process can be monitored or determined. In particular, the drying process can be terminated when the moisture of the exiting air reaches or falls below a predetermined threshold value relative to the moisture of the provided compressed air.

For the normal operation of the cleaning apparatus 3, the first fluid exit 69a of the first pressure container 61a can be coupled fluidically with one of the external connections 23, 25, 27, 29 of the test apparatus 1, preferably with the connection 23 for internal ventilation, via the first fluid connection 57a and a fluid supply line 73a, a first fluid supply switching valve 99a, and a fluid supply line 73, wherein the connection can preferably be established by means of a complementary or mating connection 75, for example by means of a plug-in nipple or a plug-in coupling. Preferably, the cleaning apparatus 3 has a temperature and/or a pressure sensor (not shown), which is thermally and/or fluidically coupled with the fluid supply line 73 to detect the temperature and/or the pressure of the supplied cleaning fluid 63 or flushing fluid 65.

Accordingly, the second fluid exit 69b of the second pressure container 61b can be coupled hydraulically with the above external connection 23 via the second fluid connection 57b and a fluid supply line 73b, a second fluid supply switching valve 99b, and the fluid supply line 73. By means of the fluid supply switching valves 99a, 99b, it can be controlled, preferably in a computer-assisted or automatic manner, whether the cleaning fluid 63 of the first pressure container 61a or the flushing fluid 65 of the second pressure container 61b is supplied to the test apparatus 1. A manual disconnection and coupling of the fluid lines is advantageously not required for that.

The cleaning apparatus 3 further comprises at least one connection 87a, 87b, 87c, 87d for a collecting container 89, which during normal operation collects the fluids exiting or flowing out of the internal volumes 35, 49, 51, 43, 47, 45, 37, 39, 41, 55, 33, $V_{11}$, $V_{12}$, $V_{13}$, $V_{14}$, $V_{15}$ of the test apparatus 1. The collecting container 89 comprises at least one fluid supply 91a, 91b, 91c, 91d and a vent 93. For the normal operation of the cleaning apparatus 3, the at least one fluid supply 91a, 91b, 91c, 91d of the collecting container 89 can be fluidically coupled with one of the external connections 23, 25, 27, 29 of the test apparatus 1 via at least one fluid discharge line 95a and one fluid discharge connection 97a, wherein the fluid discharge connection 97a is preferably a connection that is complementary to the respective external connection 23, 25, 27, 29, for example a plug-in nipple or a plug-in coupling. It is understood that also a plurality of external connections 23, 25, 27, 29 of the test apparatus 1 can be coupled with an associated fluid supply 91a, 91b, 91c, 91d of the collecting container 89 via an associated fluid discharge line 95a, 95b, 95c, 95d via fluid discharge connections 97a, 97b, 97c.

To advantageously prevent excess pressure from building up in the collecting container 89, at least one vent 93 is provided to allow the gaseous phase of the fluid supplied to the collecting container 89 and the air displaced by the fluid in the connecting container to escape into the environment. To prevent the test apparatus 1 from being contaminated by a fluid flowing back from the collecting container 89, the fluid supplies 91a, 91b, 91c, 91d are preferably provided with a check valve. Particularly preferably, the fluid supplies 91a, 91b, 91c, 91d are formed as plug-in nipples or plug-in couplings, which each have a closure valve and/or a check valve. Alternatively, a closure valve and/or a check valve can be arranged in a complementary plug-in coupling or a complementary plug-in nipple of the connections 87a, 87b, 87c, 87d of the fluid discharge lines 95a, 95b, 95c, 95d. Further preferably, a bacteria-retaining apparatus or a virus-retaining apparatus 101 is arranged downstream of the vent 93 to advantageously prevent the environment from being contaminated by pathogenic germs exiting the test apparatus. The bacteria-retaining apparatus or the virus-retaining apparatus 101 can be fluidically coupled with the vent 93 particularly by means of a retaining apparatus connection 88, particularly be fluidically coupled in a sterile manner. Preferably, the bacteria-retaining apparatus or the virus-retaining apparatus 101 is at least partially arranged within the housing 4 of the cleaning apparatus 3, as is shown in FIG. 2, wherein the retaining apparatus connection 88 is preferably arranged or formed in or on the housing 4. Alternatively, the bacteria or virus-retaining apparatus 101 can also be arranged as an external apparatus outside the housing.

To enable both the filling of the internal volumes of the test apparatus 1 with a cleaning fluid 63 or a flushing fluid 65 via the complementary connection 75 and the draining into the collecting container 89 via one of the fluid discharge connections 97d, the cleaning apparatus 3 comprises a first outlet switching valve 103, which is controlled in an opposite manner to the first and second fluid supply switching valves 99a, 99b. In this case, the complementary connection 75 and the fluid discharge connection 97d are identical and coupled with the external connection 23 for internal ventilation of the test apparatus 1. The first discharge switching valve 103 is closed when at least one of the two fluid supply switching valves 99a, 99b is opened. Contrary, the first discharge switching valve 103 is only opened when both fluid supply switching valves 99a, 99b are closed. Thus, a contamination of the cleaning fluid 63 in the pressure container 61a and of the flushing fluid 65 in the pressure container 61b by fluid flowing back can advantageously prevented.

To further enable both the supply of compressed air to the external connection 29 for the external reference tank via the fluid discharge connection 97a and the drainage into the collecting container 89, the cleaning apparatus 3 comprises a second discharge switching valve 105, which is controlled in an opposite manner to a compressed air supply switching valve 107. In other words, the second discharge switching valve 105 is closed when the compressed air supply switching valve 107 is opened, and vice versa. Thus, a contamination of the compressed air supply line 79 by fluid flowing back can advantageously be prevented.

Alternatively or in addition to the compressed air supply switching valve 107, a first bypass valve 115a can be arranged between the first fluid connection 57a and the first compressed air connection 59a for the first container 61a to enable the supply of compressed air via the external connection 23 of the test apparatus 1. Further alternatively or in addition to the compressed air supply switching valve 107 and/or the first bypass valve 115a, a second bypass valve 115b can be arranged between the second fluid connection 57b and the second compressed air connection 59b for the second container 61b to enable the supply of compressed air via the external connection 23 of the test apparatus.

Preferably, the cleaning apparatus 3 can have a hot steam supply connection 122, which can be particularly formed or arranged in or on the housing 4. The hot steam supply connection 122 is adapted to be fluidically coupled with a hot steam connection 124 of a hot steam generator 125. Hot steam generated by the hot steam generator 125 can be supplied to the cleaning apparatus 3 via the hot steam supply connection 122 and a hot steam switching valve 120. It is understood that the hot steam generator 125 can alternatively be formed within the housing 4 of the cleaning apparatus 3.

Via the compressed air supply line 79 and the compressed air supply switching valve 107, the hot steam can be supplied either directly to the test apparatus 1 via the external connection 29 or be supplied to the external connection 23 via at least one of the pressure containers 61a, 61b, the fluid supply lines 73a, 73b. Advantageously, a sterilization of the internal volumes can be performed by means of the hot steam. Particularly preferably, a sterilization of the pressure container(s) 61a, 61b can be performed by supplying hot steam via one of the pressure containers 61a, 61b or via both pressure containers 61a, 61b at the same time.

FIG. 6 shows a flow diagram of a preferred automatic, particularly computer-assisted, cleaning process with reference to FIGS. 1 and 5. It is understood that switching of the valves cannot only be performed automatically, but also manually. Preferably, a user is interactively requested to take several actions at the beginning of and optionally during the cleaning process, for example, couple tubes to specific external connections, and to subsequently confirm these actions via an input unit (not shown). Further preferably, switching of the valves is performed automatically according to a cleaning program to be selected.

Figure 7A:
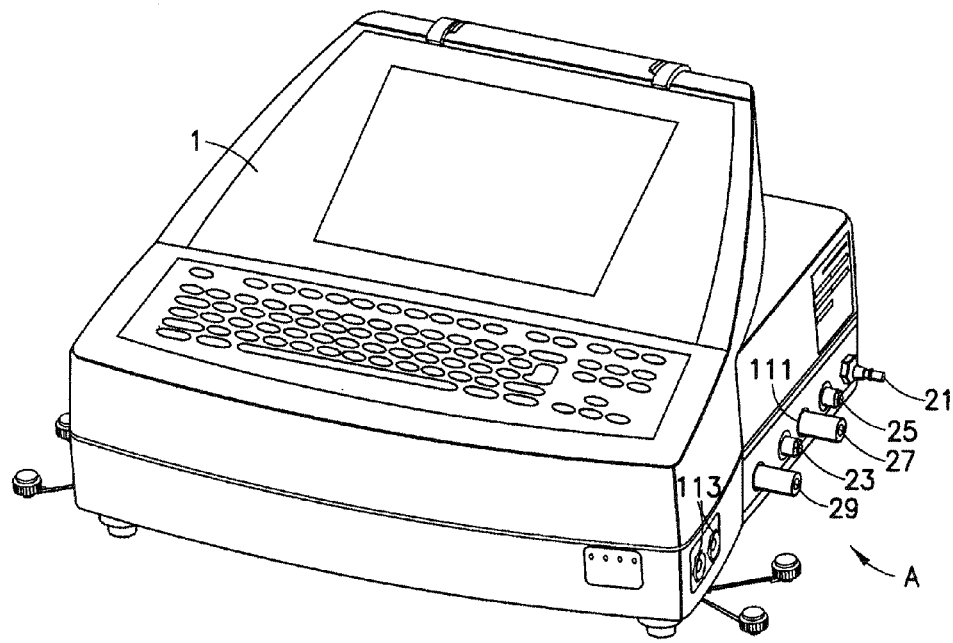
FIG. 7a a perspective view of a preferred embodiment of a test apparatus.
Figure 7B:
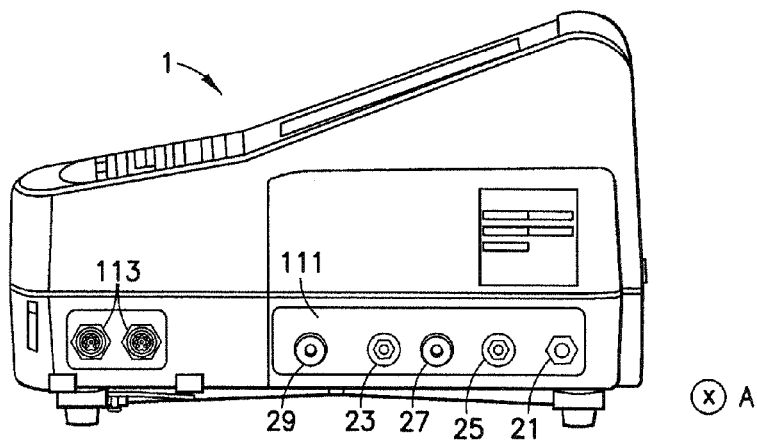
FIG. 7b a side view of the preferred embodiment of the test apparatus.

At the beginning of the cleaning process, the test apparatus 1 is preferably in a normal state, wherein the switching valves 11, 14 and the proportional valve 16 are closed and the switching valves 12, 13, 15 are open. In an initialization step S110, a first pressure container 61a is filled with a cleaning fluid 63 and a second pressure container 61b is filled with a flushing fluid 65. The compressed air intakes 67a, 67b and the fluid exits 69a, 69b of the pressure containers 61a, 61b are coupled with the associated compressed air connections 59a, 59b and fluid connections 57a, 57a, respectively, of the cleaning apparatus 3. Further preferably, the required complementary external connections 75, 84, 97a, 97b, 97c, 97d of the cleaning apparatus 3 are coupled with the associated external connections 21, 23, 25, 27, 29 of the test apparatus 1. This can preferably be done by means of a connection device 109, which can be coupled with a complementary connection device 111 (as is shown in FIGS. 7a and 7b) of the test apparatus 1. The cleaning apparatus 3 is in an initial state, wherein the compressed air valve 82, the first 99a and second 99b fluid supply switching valves, the first 103 and second 105 discharge switching valves, and the compressed air supply switching valve 107 are closed. The correct coupling of the cleaning apparatus 3 with the test apparatus 1 is confirmed by the user via the input unit, for example by actuating a start button (not shown).

The steps of the cleaning process described in the following are preferably performed automatically without any further user input. The test apparatus 1 is put into a start state for cleaning, wherein the switching valves 11, 12, 13, 14 and the proportional valve 16 are closed, while the switching valve 15 remains open (step S112).

After the cleaning process has been started, the compressed air valve 82 is opened in a step S120, so that compressed air from the compressed air source 77 gets into the pressure containers 61a, 61b via the T-connection 83, the compressed air valve 82, and the compressed air line 79. Thereby, excess pressure builds up within the pressure containers 61a, 61b, which preferably is approx. 1.1 to 2 bar, further preferably approx. 2 bar. In a step S124, the first fluid supply switching valve 99a, the switching valves 12, 13 are opened and the switching valve 15 is closed to fill the internal reference tank 33 with the cleaning fluid 63 from the pressure container 61a. In doing so, due to the excess pressure in the pressure container 61a, i.e. by pneumatic conveyance, the cleaning fluid 63 rises through the riser pipe 71a via the fluid supply lines 73a, 73 to the external connection 23 for internal ventilation of the test apparatus 1. Starting from the external connection 23, the cleaning fluid 63 flows to the internal reference tank 33 via the line 43, the switching valve 13, the lines 39, 35, 37, the switching valve 12, and the line 49. From there, the cleaning fluid 63 can flow further via the line 51 and from the external connection 29 out of the test apparatus. Filling of the internal reference tank 33 is preferably determined by means of a predetermined or predeterminable filling time T124.

Subsequently, after the internal reference tank 33 has been filled, the external connection 27, which is adapted for connection of a filter 5 or a container 7, is filled with cleaning fluid in a step S126. To this end, in step S126, the switching valve 12 is closed and the switching valve 14 is opened, so that the cleaning fluid 63 can flow to the external connection 27 via the line 35, the switching valve 14, and the line 47. Preferably, the filling process is time-controlled and thus terminated after a predetermined or predeterminable filling time T126. Finally, in a step S128, the remaining part of the internal volumes, i.e. the line 41, the switching valve 15, and the line 45, are filled with the cleaning fluid 63 after the switching valve 15 has been opened. This filling process is also terminated preferably after a predetermined or predeterminable filling time T128.

Filling of the internal volumes during the cleaning steps S124, S126, and S128 usually causes cleaning fluid 63 to exit the test apparatus 1 via the external connections 25, 27, 29. This exiting cleaning fluid 63 is lead to a collecting container 89 via the fluid discharge lines 95a, 95b, 95c connected to the external connections 25, 27, 29. Preferably, the filling times T24, T26, and T28 are such that cleaning fluid exits from all external connections 25, 27, 29 and flows to the collecting container 89, so that it is advantageously ensured that all internal volumes are filled with cleaning fluid 63 and all contaminations are already flushed out.

In a subsequent cleaning step S130, the switching valves 13, 14 are closed and the switching valve 12 is opened. In this state of the test apparatus 1, the cleaning fluid 63 resides temporarily within the internal volumes, so that contaminations can be removed from the walls of the internal volumes by soaking or dissolving by means of the cleaning fluid 63. In this state, the test apparatus pauses for a predetermined soaking time T130, which is preferably approx. 10 to approx. 60 minutes.

At the end of the cleaning process, the switching valve 12 is closed in a cleaning step S132. To drain the internal volumes filled with the cleaning fluid 63, the following measures are conducted in a step S146. The first fluid supply switching valve 99a and the second discharge switching valve 105 are closed, while the first discharge valve 103 and the compressed air supply switching valve 107 are opened. Thereby, the external connection 29 of the test apparatus 1 is supplied with compressed air via the compressed air line 79, the compressed air supply switching valve 107, and the fluid discharge line 95c. After the switching valve 12 has been opened, the excess pressure applied to the external connection 29, which is provided by the compressed air source 77, is applied to the internal volumes 51, 33, 49, $V_{12}$, 37, 35, 39, 55, so that successive draining of the internal volumes can be started with subsequently. In a step S148, the switching valve 13 is opened to drain the internal reference tank 33 via the external connection 23. The drain time T148 is preferably at least approx. 120 seconds.

To drain the internal volumes $V_{11}$, 35, 39, $V_{13}$, 43, the switching valve 12 is closed in a step S150, the switching valve 14 is opened, and the proportional valve 16 is at least partially, preferably approx. 50%, opened. The duration T150 of the pressure buildup is preferably approx. 10 seconds. After that, in the step S150, the switching valve 11 is opened, and the switching valves 13, 14 are alternatingly opened and closed, preferably for a duration of approx. 10 seconds. Further preferably, the overlap time, during which both switching valves 13, 14 are open or closed, is approx. 1 s or more. In this step S150, the cleaning fluid can be drained from the volumes of the lines 35, 39, 43, 41, 45, 47 and the volumes $V_{13}$, $V_{14}$, $V_{15}$ of the switching valves 13, 14, 15 via the external connections 23, 25, 27 into the collecting container 89.

In a subsequent step S152, the switching valves 11, 14, 15 are opened and the switching valves 12, 13 are closed, wherein the proportional valve 16 remains opened preferably approx. 50%. Now, the switching valve 15 is opened and closed in an alternating manner, preferably at intervals of approx. 10 seconds, to drain the internal volumes of the switching valve 15 and the lines 41, 45, 47 via the external connections 25, 27.

Subsequently, all switching valves 11, 13, 14, 15 except for the switching valve 12, which separates the internal reference tank 33, and the proportional valve 16 are opened to drain all external connections 23, 25, 27 except for the external connection 29 for the external reference tank 31, which has already been drained via the internal reference tank 33. After a predetermined or predeterminable drain time, all switching valves 11, 12, 14 and the proportional valve 16 are closed, while the switching valve 15, which is associated with the external vent 25, and the switching valve 13, which is associated with the internal vent 23, remain open. After the step S156 has been completed, flushing of the internal volumes is prepared.

After the test apparatus 1 has been drained, the flushing of the internal volumes of the test apparatus 1 is prepared in a step S162. The compressed air valve 82, the first discharge valve 103, and the compressed air supply switching valve 107 are closed and the second fluid supply switching valve 99b and the second discharge switching valve 105 are opened. Thereby, flushing fluid 65 from the second pressure container 61b can be pneumatically conveyed to the external connection 23 of the test apparatus 1. Subsequently, the compressed air valve 82 is opened.

To fill the internal reference tank 33, the switching valves 12, 13 are opened in a step S166. The switching valve 15 is also open, while the switching valves 11, 14 and the proportional valve 16 are closed. After a predetermined flushing time T166, the switching valve 12 is closed and the switching valve 14 is opened to fill the internal volume of the test connection 27 and the coupling line 47 with flushing fluid 65 in a step S168. After a predetermined flushing time T168, the switching valve 15 is opened to fill the internal volumes of the coupling lines 41, 45 and the switching valve 15 with the flushing fluid 65 in a step S170. Preferably, the cleaning steps S66, S68, and S170 can be repeated in an alternating manner. After that, the switching valves 12, 13, 14, 15 are opened to flush all external connections 23, 25, 27, 29 of the test apparatus 1 with the flushing fluid 65 in a step S172. The flushing fluid 65 exiting the test apparatus 1 during the flushing of the internal volumes is lead into the collecting container 89 via the fluid discharge lines 95a, 95b, 95c. At the end of the flushing process, the switching valves 11, 12, 13, 14, and 16 and the compressed air valve 82 are closed.

Preferably, after the step S172, a drainage and sterilization of the internal volumes can be performed. By analogy with steps S146 to S156, draining is performed in the steps S146' to S156'. As for the description of the steps S146' to S156' described in FIG. 6, reference is made to the previous description of the steps S146 to S156. Subsequently, sterilization can be performed by means of hot steam. For sterilization, in a step S183, the compressed air valve 82 is closed and the hot steam switching valve 120 coming from the internal or external hot steam generator 125 is opened. Preferably, at least one of the completely drained pressure containers 61a, 61b can be flown through by hot steam. To this end, preferably all internal valves 11 to 16 are closed and merely the fluid supply switching valves 99a, 99b and the first discharge switching valve 103 are open. Preferably, also the second discharge switching valve 105 and the compressed air supply switching valve 107 are opened in a period of approx. 60 seconds, preferably approx. 120 seconds, for approx. 10 seconds each in order to sufficiently sterilize the fluid discharge line 95c and the portion of the compressed air supply line 79 arranged between the compressed air supply switching valve 107 and the fluid discharge line 95c. The overall duration of the above-described step 183 of sterilizing is preferably 30 to 60 minutes. This process is optional; the pressure containers 61a, 61b might as well be autoclaved separately.

In the further course, the internal volumes of the test apparatus 1 can be sterilized. The steps S184' to S194' shown in FIG. 6 correspond to the steps of drying S184 to S194. As for the description of the steps S184' to S194' described in FIG. 6, reference is made to the previous description of the steps S184 to S194, wherein the following preferred deviation takes place: The step 184' lasts until the required sterilization temperature of approx. 121° C., preferably approx. 134° C., has been reached in the internal reference tank 33 of the test apparatus. This step then lasts for a further period of 30 to 60 minutes. It is followed by the steps 188' to 192' for a total time of preferably 30 to 60 minutes. Particularly, the temperature of the exiting fluid and/or the temperature in the internal reference tank can be monitored by means of the preferred temperature sensor in order to increase the sterilization duration and the duration of times in which the required temperature of approx. 121° C. or 134° C. is fallen below.

To drain the flushing fluid 65 from the internal volumes of the test apparatus 1 or to dry the internal volumes of the test apparatus 1, the following measures are conducted in a step S184. The second fluid supply switching valve 99b and the second discharge switching valve 105 are closed, while the first discharge valve 103 and the compressed air supply switching valve 107 are opened. Thereby, the external connection 29 of the test apparatus 1 is supplied with compressed air via the compressed air line 79, the compressed air supply switching valve 107, and the fluid discharge line 95c. In a step S186 of drying the internal volumes of the test apparatus 1, the switching valves 12, 13 are opened. After a predetermined or predeterminable drying time T86 or preferably approx. 120 seconds, the switching valve 12 is closed to suppress the flow of compressed air through the internal reference tank 33. Preferably, the switching valve 12 remains closed for a time or approx. 10 seconds. Further preferably, opening and closing of the switching valve 12 is performed in an alternating manner and further preferably repeated approx. five to fifteen times.

Subsequently, in a step S188, the switching valves 11, 12, 14 are closed and the switching valves 13, 15 are opened. Furthermore, the proportional valve 16 is opened at least partially, preferably approx. 50%. Since the switching valve 11 is closed, a pressure is build up via the compressed air supply connection 21 and the proportional valve 16. After that, the switching valve 11 is opened and then, preferably several times, the switching valves 13, 14 are opened and closed in an alternating manner. Preferably, the opening and closing times of the switching valves 13, 14 are approx. 10 seconds. Further preferably, the overlap time during which both switching valves 12, 14 are open or closed at the same time, is approx. 1 s. After a predetermined or predeterminable drying time T188 of preferably approx. 2 minutes, the cleaning step S188 is terminated.

Subsequently, the switching valves 11, 14, 15 are opened and the switching valves 12, 13 are closed. To dry the connection 25 for the external ventilation of the test apparatus 1, the switching valve 15 is alternatingly opened and closed in a step S190, wherein the opening and closing times preferably are approx. 10 seconds. After a predetermined or predeterminable drying time T190, the switching valves 11, 13, 14, 15 are opened and the switching valve 12 is closed to dry all external connections 23, 25, 29 in a step S192. At the end of the drying process, the switching valves 11, 12, 13, 14 and the proportional valve 16 are closed in a step S194. The compressed air valve 82 is also closed. The successful termination of the cleaning process can preferably be confirmed by a user.

Further preferably, the test apparatus can be put into a normal state after cleaning, in which the switching valves 11, 14 and the proportional valve 16 are closed, while the switching valves 12, 13, 15 are open.

Preferably, the cleaning process comprises the step of logging the course of the cleaning process, for example by storage on a data carrier, by generating a printout of a cleaning protocol, or by transmitting the cleaning protocol over a data line. Further preferably, the cleaning process comprises the step of determining the predetermined or predeterminable times T124, T126, T128, T130, T148, T150, T166, T168, T188, and T190, particularly by performing a test run.

The FIGS. 7a and 7b show a preferred embodiment of a test apparatus 1 with a complementary connection device 111 for connection of the connection device of the cleaning apparatus. In the illustrated embodiment, the external connections 21, 23, 25, 27, 29 of the test apparatus 1 are arranged on the complementary connection device 111 in a fixed, geometrical arrangement to each other, so that an associated or mating connection device of a cleaning apparatus can be coupled with the complementary connection device 111 in a simple manner.

Preferably, the connection device of the cleaning apparatus can be arranged on the test apparatus 1 by a displacement movement along the connection direction A, particularly by a linear displacement, such that the complementary external connections of the connection device can be fluidically coupled with the associated external connections 21, 23, 25, 27, 29 of the test apparatus 1. Advantageously, the required connections can be established quickly and erroneous connections can be avoided.

It is understood that the control of the switching means, i.e. of the valves, can be performed automatically or in a computer-assisted manner during the cleaning process described with reference to FIGS. 3 and 6. Particularly, the control of the switching means can be performed by a single, non-illustrated control unit, which may be located in the test apparatus 1 or in the cleaning apparatus 3, or via two control units in communication with each other, wherein one of the two control units is located in the test apparatus 1 and the other is located in the cleaning apparatus 3. Therefore, preferably at least one electrical connection is provided between the test apparatus 1 and the cleaning apparatus 3, particularly to transmit the control signals.

The electrical connection between the test apparatus 1 and the cleaning apparatus can preferably be established by electrically contacting or connecting at least one connector of the cleaning apparatus with an associated complementary connector 113 of the test apparatus 1. Preferably, the electrical connection can be established by displacing the cleaning apparatus along the connection direction A, particularly by a linear displacement. Particularly, the electrical connection can have an interface, for example a RS232 interface, a RS435 interface, a RJ45 interface and/or a USB interface, with which preferably a data transfer between the cleaning apparatus and the test apparatus 1 can take place. Further preferably, the electrical connection can also take care of the current supply of the cleaning apparatus. Advantageously, a power supply in the cleaning apparatus can be omitted then.

Further preferably, the complementary connection device 111 of the test apparatus 1 comprises the complementary connector 113. Accordingly, the connection device of the cleaning apparatus can comprise the connector, so that advantageously both the fluidic and the electrical connection between the test apparatus 1 and the associated cleaning apparatus can be established in a particularly simple manner by means of the connection device and the complementary connection device 111.

What is claimed is:

1. A cleaning apparatus (3) for a test apparatus (1), comprising:
    at least one fluid connection (57a) for a container (61a) for a cleaning fluid (63), wherein the fluid connection (57a) is fluidically coupled with a complementary connection (75) via a fluid supply line (73, 73a), wherein the complementary connection (75) can be fluidically coupled with an external connection (23, 25, 27, 29) of the test apparatus (1), and
    at least one fluid connection (57b) for a container (61b) for a flushing fluid (65), wherein the fluid connection (57b) is fluidically connected with the complementary connection (75) via a fluid supply line (73, 73b);
    at least one apparatus for delivering a cleaning fluid (63) and/or a flushing fluid (65) from one of the containers (61a, 61b) to the complementary connection (75);
    at least one connection (87a, 87b, 87c) for a collecting apparatus (89) for collecting the cleaning fluid (63) and/or flushing fluid (65) exiting the test apparatus (1), wherein the collecting apparatus (89) can be coupled with at least one external connection (23, 25, 27, 29) of the test apparatus (1) by means of at least one fluid discharge line (95a, 95b, 95c, 95d);
    an apparatus for providing a vaporous or gaseous cleaning fluid (63), that can be coupled with an external connection (23, 25, 27, 29) of the test apparatus (1) by means of a cleaning fluid supply line (73);
    a separating apparatus, being coupled to the cleaning apparatus (3); and
    at least one connection (87a, 87b, 87c) for the separating apparatus for separating the cleaning fluid (63) exiting the test apparatus (1) into a liquid phase and a gaseous phase,
    wherein the separating apparatus can be coupled with at least one external connection (23, 25, 27, 29) of the test apparatus (1) by means of a fluid discharge line (95a, 95b, 95c, 95d), and
    wherein the liquid phase arising in the separating apparatus is collectable in a collecting container (89), and the gaseous phase arising in the separating apparatus escapes into the environment.

2. The cleaning apparatus (3) of claim 1, having at least one switching means (99a, 99b, 103, 105, 107) controlling the fluid flow through one of the fluid supply lines (73a, 73b) or controlling the fluid flow through one of the at least one fluid discharge lines (95a, 95b, 95c, 95d).

3. The cleaning apparatus (3) of claim 1, wherein the apparatus for delivering the cleaning fluid (63) or the flushing fluid (65) can be operated with compressed air or pressurized gas.

4. The cleaning apparatus (3) of claim 1, wherein the apparatus for providing the cleaning fluid comprises a hot steam generator generating a hot steam having a temperature of greater than approx. 121° C.

5. The cleaning apparatus (3) of claim 1, further comprising:
    a bacteria-retaining apparatus (101) and/or a virus-retaining apparatus (101), via which the gaseous phase escapes into the environment.

6. The cleaning apparatus (3) of claim 1, having an apparatus for providing compressed air, wherein the compressed air can be supplied to the compressed air supply connection (21) of the test apparatus (1) via a compressed air supply line connection (84).

7. The cleaning apparatus (3) of claim 6, wherein the apparatus for providing compressed air is pneumatically coupled with the apparatus for delivering the cleaning fluid (63) or the flushing fluid (65).

8. The cleaning apparatus (3) of claim 1, having a connection device (109) comprising at least two complementary external connections (59, 75, 84, 97*a*, 97*b*, 97*c*, 97*d*) of the cleaning apparatus (3).

* * * * *